US011566050B2

(12) United States Patent
Lindesmith et al.

(10) Patent No.: US 11,566,050 B2
(45) Date of Patent: Jan. 31, 2023

(54) METHODS AND COMPOSITIONS FOR NOROVIRUS VACCINES AND DIAGNOSTICS

(71) Applicant: The University of North Carolina at Chapel Hill, Chapel Hill, NC (US)

(72) Inventors: Lisa Chon Lindesmith, Apex, NC (US); Ralph Steven Baric, Haw River, NC (US); Kari Moore Debbink, Ann Arbor, MI (US); Eric Francis Donaldson, Durham, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/756,740

(22) PCT Filed: Oct. 18, 2018

(86) PCT No.: PCT/US2018/056508
§ 371 (c)(1),
(2) Date: Apr. 16, 2020

(87) PCT Pub. No.: WO2019/079594
PCT Pub. Date: Apr. 25, 2019

(65) Prior Publication Data
US 2021/0371468 A1     Dec. 2, 2021

Related U.S. Application Data

(60) Provisional application No. 62/574,012, filed on Oct. 18, 2017.

(51) Int. Cl.
| *C07K 14/005* | (2006.01) |
| *A61P 31/14* | (2006.01) |
| *A61K 39/12* | (2006.01) |
| *G01N 33/569* | (2006.01) |

(52) U.S. Cl.
CPC ............ *C07K 14/005* (2013.01); *A61K 39/12* (2013.01); *A61P 31/14* (2018.01); *G01N 33/56983* (2013.01); *C12N 2770/16022* (2013.01); *C12N 2770/16023* (2013.01); *C12N 2770/16034* (2013.01); *C12N 2770/36142* (2013.01); *G01N 2333/08* (2013.01)

(58) Field of Classification Search
None
See application file for complete search history.

(56) References Cited

U.S. PATENT DOCUMENTS

| 4,501,729 | A | 2/1985 | Boucher et al. |
| 7,527,801 | B2 | 5/2009 | Coit et al. |
| 7,862,829 | B2 | 1/2011 | Johnston et al. |
| 9,975,923 | B2 * | 5/2018 | Baric ............... G01N 33/56983 |

FOREIGN PATENT DOCUMENTS

| EP | 2324113 | 2/2018 |
| WO | 9400153 A1 | 1/1994 |
| WO | 9517210 A1 | 6/1995 |
| WO | 9633739 A1 | 10/1996 |
| WO | 2014145245 | 9/2014 |

OTHER PUBLICATIONS

Gen Bank Accession AFK75854, capsid protein [Norovirus Hu/GII. Mar. 1999], 2012.*
Chen et al. "Bioinformatics analysis of the epitope regions for norovirus capsid protein" BMC Bioinformatics, 14(Suppl. 4):55, pp. 1-6 (2012).
Debbink et al. "Chimeric GII.4 Norovirus Virus-Like-Particie-Based Vaccines Induce Broadly Blocking Immune Responses" Journal of Virology, 88(13):7256-7266 (2014).
International Search Report and the Written Opinion of the International Searching Authority corresponding to International Patent Application No. PCT/US2018/056508 (10 pages) (dated Jan. 24, 2019).
Lindesmith et al. "Particle Conformation Regulates Antibody Access to a Conserved GII.4 Norovirus Blockade Epitope" Journal of Virology, 83(16):8826-8842 (2014).
UniProtKB/TrEMBL database sequence of I3V9L9 (1 page) (2012).
Adeyemi et al. "Increasing Type 1 Poliovirus Capsid Stability by Thermal Selection" Journal of Virology, 91(4): e01586-16 (2017).
Allen et al. "Analysis of Amino Acid Variation in the P2 Domain of the GII-4 Norovirus VP1 Protein Reveals Putative Variant-Specific Epitopes" PLoS One, 3(1):e1485 (2008).
Bok et al. "Evolutionary Dynamics of GII.4 Noroviruses over a 34-Year Period" Journal of Virology, 83 (22):11890-11901 (2009).
Brimacombe et al. "Neutralizing Antibody-Resistant Hepatitis C Virus Cell-to-Cell Transmission" Journal of Virology, 85(1):596-605 (2011).
Cannon et al. "Herd Immunity to GII.4 Noroviruses Is Supported by Outbreak Patient Sera" Journal of Virology, 83 (11):5363-5374 (2009).
Carmona-Vicente et al. "Characterization of a Novel Conformational GII.4 Norovirus Epitope: Implications for Norovirus-Host Interactions" Journal of Virology, 90(17):7703-7714 (2016).
Das et al. "Defining influenza A virus hemagglutinin antigenic drift by sequential monoclonal antibody selection" Cell Host & Microbe, 13(3):314-323 (2013).
Debbink et al. "Genetic Mapping of a Highly Variable Norovirus GII.4 Blockade Epitope: Potential Role in Escape from Human Herd Immunity" Journal of Virology, 86(2):1214-1226 (2011).
Debbink et al. "Human Norovirus Detection and Production, Quantification, and Storage of Virus-Like Particles" Current Protocols in Microbiology, 31(1):15K.1.1-15K.1.45 (2013).
Debbink et al. "Within-Host Evolution Results in Antigenically Distinct GII.4 Noroviruses" Journal of Virology, 88 (13):7244-7255 (2014).
Donaldson et al. "Viral shape-shifting: norovirus evasion of the human immune system" Nature Reviews Microbiology, 8:231-241 (2010).

(Continued)

*Primary Examiner* — Benjamin P Blumel
(74) *Attorney, Agent, or Firm* — Myers Bigel, P.A.

(57) ABSTRACT

The present invention is directed to methods and compositions for norovirus therapeutics, such as vaccines, and diagnostics.

33 Claims, 14 Drawing Sheets
Specification includes a Sequence Listing.

(56) References Cited

OTHER PUBLICATIONS

Dowd et al. "A Dynamic Landscape for Antibody Binding Modulates Antibody-Mediated Neutralization of West Nile Virus" PLoS Pathogens, 7(6):e1002111 (2011).
Dowd et al. "Antibody-mediated neutralization of flaviviruses: A reductionist view" Virology, 411(2):306-315 (2011).
Ettayebi et al. "Replication of human noroviruses in stem cell-derived human enteroids" Science, 353 (6306):1387-1393 (2016).
Francica et al. "Steric Shielding of Surface Epitopes and Impaired Immune Recognition Induced by the Ebola Virus Glycoprotein" PLoS Pathogens, 6(9):e1001098 (2010).
GenBank Accession No. AAK50355.1 "capsid protein [Human calicivirus Hu/NLV/GII/MD145-12/1987/US]" NCBI.gov (1 page) (Jan. 29, 2002).
GenBank Accession No. AAZ31376.2 "capsid protein [Norovirus Hu/GII.4/Hunter 284E/04O/AU]" NCBI.gov (2 pages) (Jul. 26, 2016).
GenBank Accession No. ACT76139.1 "VP1 [Norovirus Hu/GII.4/CHDC5191/1974/US]" NCBI.gov (2 pages) (Nov. 2, 2009).
GenBank Accession No. ACX31885.1 "major capsid protein [Norovirus Hu/GII.4/Armidale/NSW390I/2008/AU]" NCBI.gov (2 pages) (Feb. 6, 2012).
GenBank Accession No. ADD10375.1 "major capsid protein [Norovirus Hu/GII.4/New Orleans1805/2009/USA]" NCBI.gov (2 pages) (Aug. 18, 2011).
GenBank Accession No. AFJ04707.1 "major capsid protein [Norovirus Hu/GII.4/1997/USA]" NCBI.gov (2 pages) (May 8, 2012).
GenBank Accession No. AFJ04708.1 "major capsid protein [Norovirus Hu/GII.4/Farmington Hills/2004/USA]" NCBI.gov (2 pages) (May 8, 2012).
GenBank Accession No. AFJ04709.1 "major capsid protein [Norovirus Hu/GII.4/Minerva/2006/USA]" NCBI.gov (2 pages) (May 8, 2012).
GenBank Accession No. AFV08795.1 "VP1 [Norovirus Hu/GII.4/Sydney/NSW0514/2012/AU]" NCBI.gov (2 pages) (May 10, 2013).
GenBank Accession No. BAE98194.1 "capsid protein [Norovirus Hu/Sakai/04-179/2005/JP]" NCBI.gov (2 pages) (Jul. 14, 2016).
GenBank Accession No. BAH30707.1 "capsid protein [Norovirus Hu/GII.4/Stockholm/19865/2008/SE]" NCBI.gov (2 pages) (Mar. 31, 2009).
GenBank Accession No. BAH56690.1 "capsid protein, partial [Norovirus Hu/GII.4/cruiseship/2007/ZAF]" NCBI.gov (2 pages) (Jul. 24, 2016).
GenBank Accession No. JQ743333.1 "Norovirus Hu/GII.3/1999 capsid protein gene, complete cds" NCBI.gov (2 pages) (Jun. 4, 2012).
Harada et al. "Driving HIV-1 into a Vulnerable Corner by Taking Advantage of Viral Adaptation and Evolution" Frontiers in Microbiology, 8(390):1-8 (2017).
International Preliminary Report on Patentability corresponding to International Patent Application No. PCT/US2018/056508 (7 pages) (dated Apr. 30, 2020).
Kaminski et al. "Antibodies against conserved antigens provide opportunities for reform in influenza vaccine design" Frontiers in Immunology, 2(76):1-14 (2011).
Kwong et al. "HIV-1 and influenza antibodies: seeing antigens in new ways" Nature Immunology, 10(6):573-578 (2009).
Kwong et al. "HIV-1 evades antibody-mediated neutralization through conformational masking of receptor-binding sites" Nature, 420(6916):678-682 (2002).
Lee et al. "The Fc Region of an Antibody Impacts the Neutralization of West Nile Viruses in Different Maturation States" Journal of Virology, 87(24):13729-13740 (2013).
Lin et al. "Conformational Shift of a Major Poliovirus Antigen Confirmed by Immuno-Cryogenic Electron Microscopy" Journal of Immunology, 191(2):1-19 (2013).

Lindesmith et al. "Broad Blockade Antibody Responses in Human Volunteers after Immunization with a Multivalent Norovirus VLP Candidate Vaccine: Immunological Analyses from a Phase I Clinical Trial" PLoS Medicine, 12(3): e1001807 (2015).
Lindesmith et al. "Emergence of a Norovirus GII.4 Strain Correlates with Changes in Evolving Blockade Epitopes" Journal of Virology, 87(5):2803-2813 (2013).
Lindesmith et al. "Immunogenetic Mechanisms Driving Norovirus GII.4 Antigenic Variation" PLoS Pathogens, 8(5): e1002705 (2012).
Lindesmith et al. "Mechanisms of GII.4 Norovirus Persistence in Human Populations" PLoS Medicine, 5(2):e31 (2008).
Lindesmith et al. "Monoclonal Antibody-Based Antigenic Mapping of Norovirus GII.4-2002" Journal of Virology, 86 (2):873-883 (2012).
Lindesmith et al. "Norovirus GII.4 Strain Antigenic Variation" Journal of Virology, 85(1):231-242 (2011).
Meloen et al. "Mimotopes: realization of an unlikely concept" Journal of Molecular Recognition, 13:352-359 (2000).
Pal et al. "Immunization with the Chlamydia trachomatis major outer membrane protein, using adjuvants developed for human vaccines, can induce partial protection in a mouse model against a genital challenge" Vaccine, 24 (6):766-775 (2005).
Patel et al. "Systematic Literature Review of Role of Noroviruses in Sporadic Gastroenteritis" Emerging Infectious Diseases, 14(8):1224-1231 (2008).
Prentoe et al. "Hypervariable region 1 shielding of hepatitis C virus is a main contributor to genotypic differences in neutralization sensitivity" Hepatology, 64(6):1881-1892 (2016).
Quiñones-Parra et al. "Universal immunity to influenza must outwit immune evasion" Frontiers in Microbiology, 5 (285):1-11 (2014).
Reeck et al. "Serological correlate of protection against norovirus-induced gastroenteritis" Journal of Infectious Diseases, 202(8):1212-1218 (2010).
Rodrigues et al. "Whither vaccines?" Journal of Infection, 74(Supplement 1):S2-S9 (2017).
Sabo et al. "Hepatitis C virus epitope exposure and neutralization by antibodies is affected by time and temperature" Virology, 422(2):174-184 (2012).
Scharf et al. "Broadly Neutralizing Antibody 8ANC195 Recognizes Closed and Open States of HIV-1 Env" Cell, 162 (6):1379-1390 (2015).
Schorn et al. "Chronic norovirus infection after kidney transplantation: molecular evidence for immune-driven viral evolution" Clinical Infectious Diseases, 51(3):307-314 (2010).
Shanker et al. "Structural Analysis of Histo-Blood Group Antigen Binding Specificity in a Norovirus GII.4 Epidemic Variant: Implications for Epochal Evolution" Journal of Virology, 85(17):8635-8645 (2011).
Siebenga et al. "Epochal Evolution of GGII.4 Norovirus Capsid Proteins from 1995 to 2006" Journal of Virology, 81 (18):9932-9941 (2007).
Singharoy et al. "Epitope Fluctuations in the Human Papillomavirus Are Under Dynamic Allosteric Control: A Computational Evaluation of a New Vaccine Design Strategy" Journal of the American Chemical Society, 135 (49):18458-18468 (2013) (Abstract Only).
Strauss et al. "Cryo-electron Microscopy Structures of Expanded Poliovirus with VHHs Sample the Conformational Repertoire of the Expanded State" Journal of Virology, 91(3):1-16 (2017).
Tan et al. "Norovirus P Particle, a Novel Platform for Vaccine Development and Antibody Production" Journal of Virology, 85(2):753-764 (2011).
Tate et al. "Playing Hide and Seek: How Glycosylation of the Influenza Virus Hemagglutinin Can Modulate the Immune Response to Infection" Viruses, 6(3):1294-1316 (2014).
Tyle, Praveen "Iontophoretic Devices for Drug Delivery" Pharmaceutical Research, 3(6):318-326 (1986).
Wu et al. "A perspective on the structural and functional constraints for immune evasion: insights from the influenza virus" Journal of Molecular Biology, 429(17):2694-2709 (2017).
Wu et al. "Autophagy-associated dengue vesicles promote viral transmission avoiding antibody neutralization" Scientific Reports, 6(32243):1-10 (2016).

(56) References Cited

OTHER PUBLICATIONS

Zarnitsyna et al. "Masking of antigenic epitopes by antibodies shapes the humoral immune response to influenza" Philosophical Transactions of the Royal Society of London Series B, Biological Sciences, 370(1676):1-10 (2015).
Zhou et al. "Quantification of the Impact of the HIV-1-Glycan Shield on Antibody Elicitation" Cell Reports, 19 (4):719-732 (2017).

* cited by examiner

| Capsid Residue | 17 | 928 | 268 | 269 | 287 | 296 | 292 | 294 | 381 | 356 | 377 | 389 | 393 | 390 | 407 | 412 | 423 | 425 | 426 | GII.4F mAb EC50 < 0.2 µg/ml |
|---|---|---|---|---|---|---|---|---|---|---|---|---|---|---|---|---|---|---|---|---|
| Day 1 | N | S | V | T | A | T | E | V | R | V | H | S | R | D | G | V | N | D | G | S | F | E | + |
| Day 581 | S | G | I | I | E | S | V | K | S | A | E | N | K | N | S | E | D | G | I | T | Y | D | – |
| 581.Day1 | N | S | V | T | A | T | E | V | R | V | H | S | R | D | G | V | N | D | G | S | F | E | + |
| 581.F1 | S | G | I | I | E | S | V | K | N | V | E | N | K | N | C | E | X | G | I | T | Y | D | – |
| 581.F2 | S | S | V | I | E | T | V | R | A | E | S | R | D | S | V | D | G | G | S | F | E | + |
| 581.F3 | N | G | V | T | A | S | V | V | S | A | E | N | K | D | S | V | D | G | G | T | F | E | + |
| 581.F4 | S | S | V | I | E | S | V | V | R | N | E | R | N | S | V | D | G | I | T | Y | D | + |
| 581.FX | S | G | I | I | E | S | V | V | G | A | E | N | K | D | S | Q | S | V | D | G | I | T | F | E | + |
| 581.F9 | S | G | I | I | E | S | V | K | R | A | E | N | K | Q | S | V | D | G | I | T | Y | D | + |
| 581.F10 | S | G | I | I | E | S | V | K | R | A | E | N | K | N | S | E | D | G | I | T | Y | D | – |
| 581.F11 | S | G | I | I | E | S | V | R | A | E | N | K | N | S | V | D | G | I | T | Y | D | + |
| 581.F12 | S | G | I | I | E | S | V | S | A | E | N | K | N | S | V | D | G | I | T | Y | D | + |
| 581.F | S | G | I | I | E | S | V | S | A | E | N | K | N | S | V | D | G | I | T | Y | D | + |
| 2002.581F | N | G | V | T | A | T | N | K | G | V | H | N | K | D | N | E | S | T | G | F | P | E | – |
| 2002 | N | G | V | T | A | T | N | V | G | V | H | N | K | D | N | V | S | T | G | F | P | E | + |

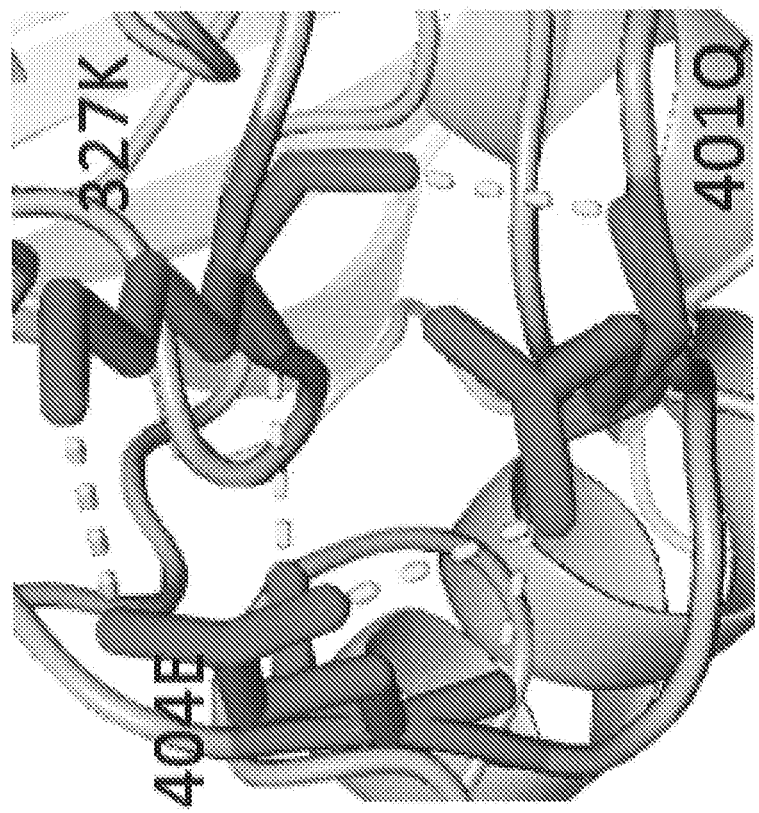
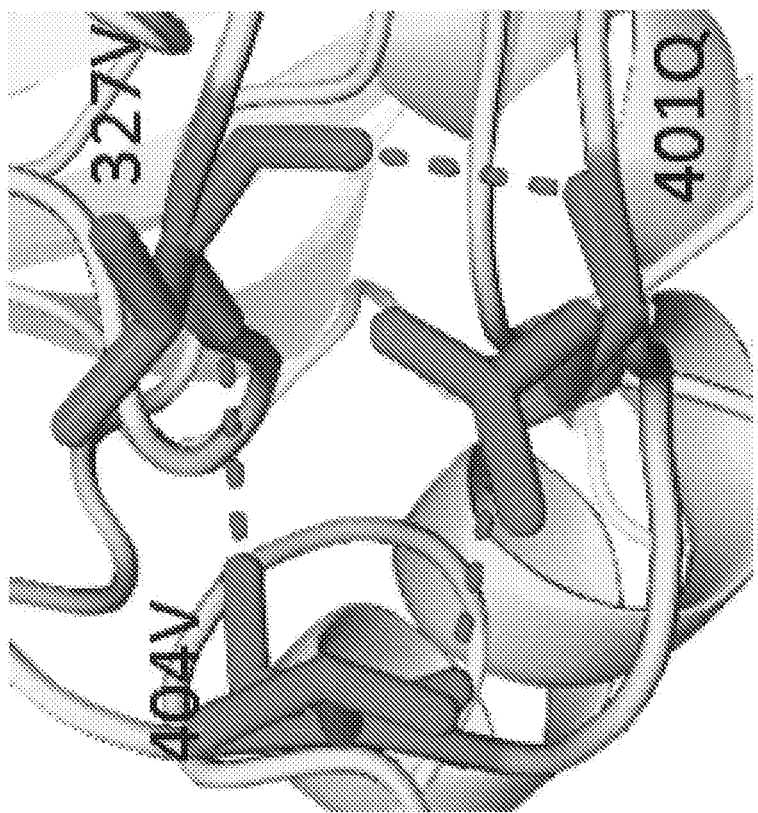
FIG. 3

| Capsid Residue | 234 | 327 | 340 | 391 | 404 | GII.4F mAb Bmax $OD_{450nm}$ (95% Confidence Interval) | GII.4F mAb $K_D$, nM (95% Confidence interval) |
|---|---|---|---|---|---|---|---|
| 581.FX | V | V | G | D | V | 0.9538, (0.9093-1) | 1.14 (0.91-1.43) |
| 581.F12 | V | V | S | N | V | 0.8486, (0.8001-0.8996) | 1.06 (0.81-1.40) |
| 581.F | I | V | S | N | V | 0.5482, (0.5252-0.572) | 1.20 (0.99-1.46) |
| 581.F9 | V | K | G | D | E | < LOD | < LOD |
| Day 581 | I | K | S | N | E | < LOD | < LOD |
| GII.4F Epitope | - | + | - | - | + | | |
| GII.4F Access | + | + | - | - | + | | |

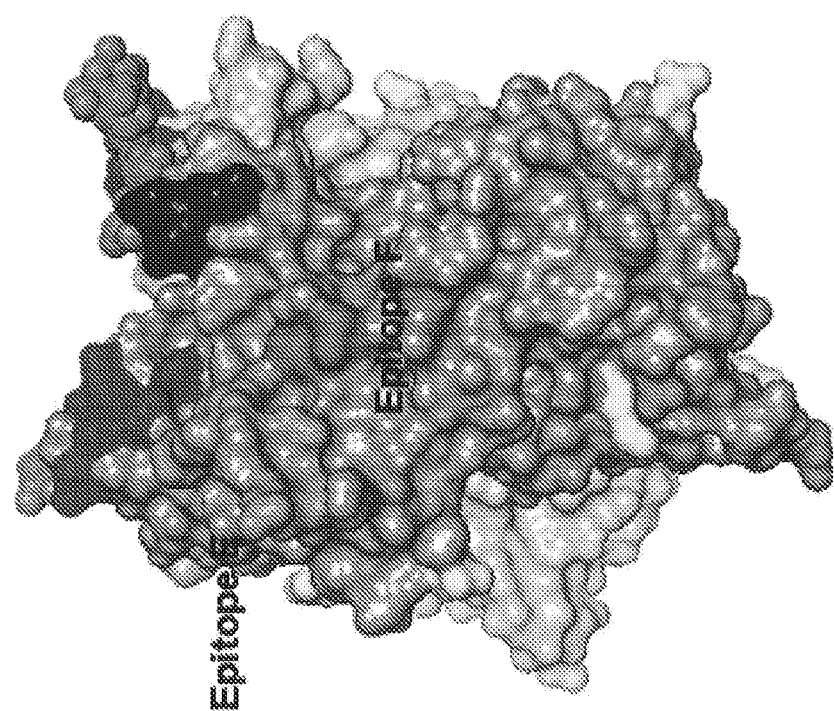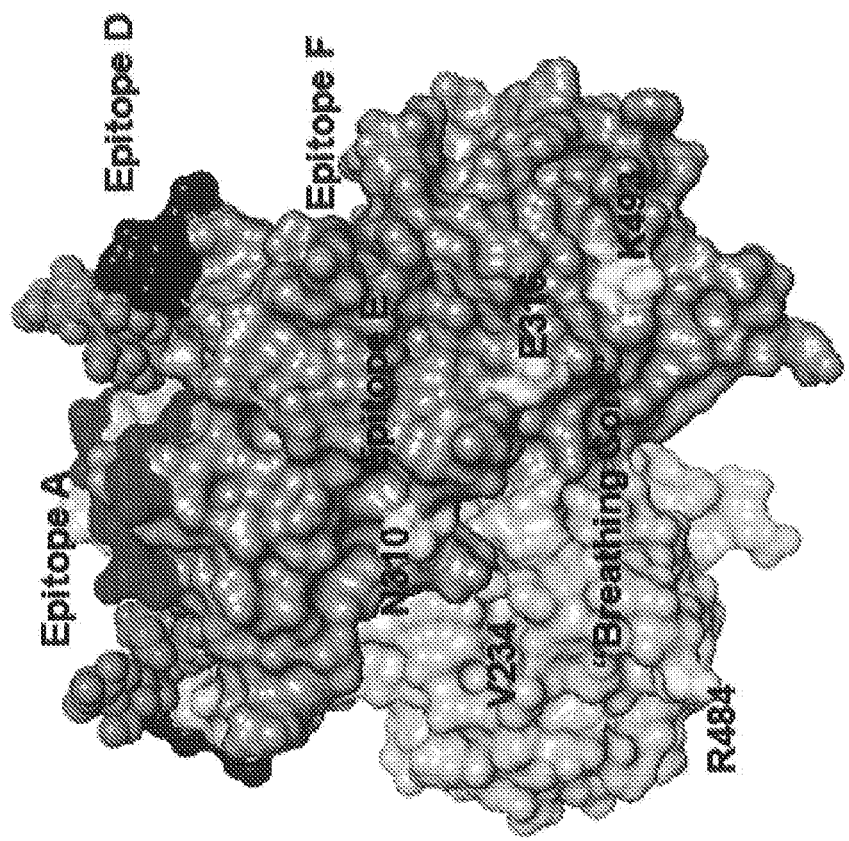
FIG. 5

| Capsid Residue | 3 2 7 | 3 4 0 | 3 7 2 | 3 7 7 | 4 1 2 | 4 1 3 | GII.4E mAb Bmax OD$_{450nm}$ (95% Confidence Interval) | GII.4E mAb K$_D$ nM (95% Confidence Interval) |
|---|---|---|---|---|---|---|---|---|
| 581 | K | E | D | G | D | I | <LOD | <LOD |
| 581.2002E | K | E | S | T | G | G | <LOD | <LOD |
| 581.F | V | V | D | G | D | I | <LOD | <LOD |
| 581.2002E/F | V | V | S | T | G | G | 0.528 (0.4688-0.5942) | 1.22 (0.70-2.13) |
| 2002.581F | K | E | S | T | G | G | 1.523 (1.432-1.618) | 0.33 (0.24-0.46) |
| 2002 | V | V | S | T | G | G | 1.878 (1.778-1.982) | 0.16 (0.12-0.20) |
| GII.4E mAb

FIG. 7

| Epitope | A | | | | | | | B | | C | | D | | | | E | | | F | | | | | Fs | |
|---|---|---|---|---|---|---|---|---|---|---|---|---|---|---|---|---|---|---|---|---|---|---|---|---|---|
| Amino Acids | 294 | 296 | 297 | 298 | 368 | 372 | 373 | 333 | 382 | 340 | 376 | 391 | 393 | 394 | 395 | 406 | 411 | 412 | 234 | 310 | 316 | 483 | 492 | 327 | 403 |
| GII.4.1974 (SEQ ID NO:1) | G | S | H | D | T | N | N | L | K | A | Q | D | D | H | H | N | S | G | V | N | E | R | K | V | V |
| GII.4.1987 (SEQ ID NO:2) | V | S | H | D | T | N | N | L | K | A | Q | D | D | H | H | N | T | G | V | N | E | R | K | V | V |
| GII.4.1997 (SEQ ID NO:3) | A | S | H | D | T | N | N | M | K | E | Q | D | G | N | H | N | T | G | V | N | E | R | K | V | V |

*FIG. 10A*

| Epitope | A | | | | | | | B | | C | | D | | | | | | E | | | F | | | | | Fs | |
|---|---|---|---|---|---|---|---|---|---|---|---|---|---|---|---|---|---|---|---|---|---|---|---|---|---|---|---|
| Amino Acids | 294 | 296 | 297 | 298 | 368 | 372 | 373 | 333 | 382 | 340 | 376 | 391 | 393 | 394 | 395 | 396 | 407 | 412 | 413 | 234 | 310 | 316 | 484 | 493 | 327 | 404 |
| GII.4.2002 (SEQ ID NO:4) | A | T | H | N | N | N | N | M | K | G | E | D | N | G | A | H | S | T | G | V | N | E | R | K | V | V |
| GII.4.2002a (SEQ ID NO:5) | A | T | H | N | N | N | N | M | K | G | E | D | N | G | T | H | S | T | G | V | N | E | R | K | V | V |
| GII.4.2004 (SEQ ID NO:6) | A | A | Q | N | S | S | N | V | R | R | E | D | S | T | T | H | D | D | S | V | N | E | R | K | V | V |
| GII.4.2005 (SEQ ID NO:7) | P | T | R | T | A | D | N | M | R | G | E | D | S | S | A | H | D | T | V | V | N | E | R | K | V | V |
| GII.4.2006 (SEQ ID NO:8) | A | S | R | N | S | E | N | V | K | G | E | D | S | T | T | H | S | N | V | V | N | E | R | K | V | V |
| GII.4.2007 (SEQ ID NO:9) | A | T | Q | E | S | S | N | V | R | R | E | D | S | T | T | H | N | D | S | V | N | E | R | K | V | V |
| GII.4.2008a (SEQ ID NO:10) | A | S | R | N | A | D | N | M | K | S | E | D | S | T | T | H | N | T | G | V | N | E | R | K | V | V |
| GII.4.2008s (SEQ ID NO:11) | S | S | R | N | A | D | N | V | K | A | D | D | N | T | A | H | S | N | S | V | S | E | R | K | V | V |
| GII.4.2009 (SEQ ID NO:12) | P | S | R | N | A | D | N | V | K | T | E | D | S | T | T | P | S | N | I | V | S | E | R | K | V | V |
| GII.4.2012 (SEQ ID NO:13) | T | S | R | N | E | D | R | V | K | T | E | D | G | T | T | H | S | N | T | V | D | E | R | K | V | V |

*FIG. 10B*

| Capsid Residue | 391 | 393 | 394 | 395 | 396 | NVB 97 Half-Max, μg/ml (95% CI) | NO66 Half-Max, μg/ml (95% CI) | NO224 Half-Max, μg/ml (95% CI |
|---|---|---|---|---|---|---|---|---|
| GII.4 2009 | D | S | T | T | P | 0.05 (0.04-0.06) | 0.07 (0.07-0.08) | 0.05 (0.05-0.06) |
| GII.4 2012 | D | G | T | T | H | >2 | 0.65 (0.60-0.71) | 0.18 0.16-0.20) |
| GII.4 2012.09D | D | S | T | T | P | >2 | 0.06 (0.05-0.07) | 0.03 (0.03-0.03) |
| GII.4 2012 G393S | D | S | T | T | H | 0.24 (0.22-0.26) | **.62 (0.56-0.69)** | 0.12 (0.11-0.14) |
| GII.4 2012 H396P | D | G | T | T | P | >2 | **.05 (0.04-0.06)** | 0.03 (0.02-0.03) |
| Epitope Anchor Residue | | | | | | D 393 | D 396 | Undefined Near D |

*FIG. 12*

METHODS AND COMPOSITIONS FOR NOROVIRUS VACCINES AND DIAGNOSTICS

STATEMENT OF PRIORITY

This application is a 35 U.S.C. § 371 national phase application of International Application Serial No. PCT/US2018/056508, filed Oct. 18, 2018, which claims the benefit, under 35 U.S.C. § 119(e), of U.S. Provisional Application No. 62/574,012, filed Oct. 18, 2017, the entire contents of each of which are incorporated by reference herein.

STATEMENT OF GOVERNMENT SUPPORT

This invention was made with government support under Grant Nos. AI056531, AI106006 and AI109761 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-824_ST25.txt, 66,100 bytes in size, generated on Apr. 10, 2020 and filed via EFS-Web, is provided in lieu of a paper copy. This Sequence Listing is hereby incorporated herein by reference into the specification for its disclosures.

FIELD OF THE INVENTION

This invention is directed to methods and compositions for norovirus therapeutics, such as vaccines, and diagnostics.

BACKGROUND OF THE INVENTION

Antigenic diversity is a hallmark of many successful RNA viruses. However, requirements for structure integrity and maintenance of key capsid functions such as receptor binding and cell fusion require essential residues to remain conserved over time, representing potential cross-protective antibody (Ab) epitopes. To combat this weakness, many human RNA viruses including seasonal influenza, human immunodeficiency, hepatitis C, Ebola, West Nile and human norovirus (NoV) have evolved strategies to camouflage neutralizing antigenic sites. Local mechanisms of camouflage include shielding of the epitope with carbohydrates or lipids or by structurally occluding the site by burying the epitopes beneath the surface topology. Other mechanisms include "particle breathing," described as dynamic conformational changes in the virion that limit antibody access to occluded epitopes. Effective use of these evasive mechanisms provides an advantage to viruses with high population exposure, including human norovirus.

Human NoV is the leading cause of acute gastroenteritis and causes more than 21 million infections per year in the United States and approximately 200,000 deaths worldwide, primarily in the young and aged populations. This heavy disease burden on particularly vulnerable populations warrants development of a NoV vaccine. The primary obstacle to a successful vaccine is the extensive antigenic diversity between NoV strains and within the pandemic GII.4 strains. Like influenza A virus, the major capsid sequence of the norovirus GII.4 strains is undergoing epochal evolution resulting in emergent immune escape variants every 2-5 years.

The present invention overcomes previous shortcomings in the art by providing methods and compositions for norovirus therapeutics, including multivalent vaccines, and diagnostics.

SUMMARY OF THE INVENTION

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

In one embodiment, the present invention provides a chimeric norovirus capsid protein consisting of a norovirus VP1 major capsid protein backbone from norovirus strain GII.4.1974 (SEQ ID NO:1), norovirus strain GII.4.1987 (SEQ ID NO:2), norovirus strain GII.4.1997 (SEQ ID NO:3), norovirus strain GII.4.2002 (SEQ ID NO:4), norovirus strain GII.4.2002a (SEQ ID NO:5), norovirus strain GII.4.2004 (SEQ ID NO:6), norovirus strain GII.4.2005 (SEQ ID NO:7), norovirus strain GII.4.2006 (SEQ ID NO:8), norovirus strain GII.4.2007 (SEQ ID NO:9), norovirus strain GII.4.2008a (SEQ ID NO:10), norovirus strain GII.4.2008s (SEQ ID NO:11), norovirus strain GII.4.2009 (SEQ ID NO:12), or norovirus strain GII.4.2012 (SEQ ID NO:13) in which two or more, in any combination, of the following sets of amino acid residues (a)-(k): a) amino acid residues 294, 296, 297, 298, 368 and 372 (Epitope A); b) amino acid residues 333 and 382 (Epitope B); c) amino acid residues 340 and 376 (Epitope C); d) amino acid residues 391, 393, 394, 395 and 396 (Epitope D); e) amino acid residues 407, 412 and 413 (Epitope E); f) amino acid residues 234, 310, 316, 484 and 493 (Epitope F); and g) amino acid residues 327 and 404 (Epitope Fs), wherein amino acid residue numbering of (a)-(g) is based on the amino acid sequence of any of SEQ ID NOs:4-13; and h) amino acid residues 391, 393, 394 and 395 (Epitope D); i) amino acid residues 406, 411 and 412 (Epitope E); j) amino acid residues 234, 310, 316, 483 and 492 (Epitope F), and k) amino acid residues 327 and 403 (Epitope Fs), wherein amino acid residue numbering of (h)-(k) is based on the amino acid sequence of SEQ ID NOs:1-3, are substituted into the capsid protein backbone to introduce at least one epitope from each of two or more different norovirus strains of the above norovirus strains, each of which is different from one another and each of which is different from the norovirus strain of the capsid protein backbone.

In another embodiment, the present invention provides a chimeric norovirus capsid protein consisting of a norovirus VP1 major capsid protein backbone from norovirus strain GII.4.1974 (SEQ ID NO:1), norovirus strain GII.4.1987 (SEQ ID NO:2), norovirus strain GII.4.1997 (SEQ ID NO:3), norovirus strain GII.4.2002 (SEQ ID NO:4), norovirus strain GII.4.2002a (SEQ ID NO:5), norovirus strain GII.4.2004 (SEQ ID NO:6), norovirus strain GII.4.2005 (SEQ ID NO:7), norovirus strain GII.4.2006 (SEQ ID NO:8), norovirus strain GII.4.2007 (SEQ ID NO:9), norovirus strain GII.4.2008a (SEQ ID NO:10), norovirus strain GII.4.2008s (SEQ ID NO:11), norovirus strain GII.4.2009 (SEQ ID NO:12), or norovirus strain GII.4.2012 (SEQ ID NO:13) in which amino acid residues 234, 310, 316, 484 and 493 (Epitope F), wherein amino acid residue numbering is based on the amino acid sequence of any of SEQ ID NOs:4-13 or amino acid residues 234, 310, 316, 483 and 492 (Epitope F), wherein amino acid residue numbering is based on the amino acid sequence of any of SEQ ID NOs:1-3, are substituted into the capsid protein backbone to introduce Epitope F from a norovirus strain that is different from the norovirus strain of the capsid protein backbone.

In a further embodiment, the present invention provides a synthetic backbone molecule comprising two or more sets of amino acid residues wherein each set of amino acid residues forms a norovirus conformational epitope, wherein the two or more sets of amino acid residues each form a conformational epitope from two or more norovirus strains that are different from one another and wherein the two or more sets of amino acid residues are selected in any combination from the group consisting of the following sets of amino acid residues (a)-(k): a) amino acid residues 294, 296, 297, 298, 368 and 372 (Epitope A); b) amino acid residues 333 and 382 (Epitope B); c) amino acid residues 340 and 376 (Epitope C); d) amino acid residues 391, 393, 394, 395 and 396 (Epitope D); e) amino acid residues 407, 412 and 413 (Epitope E); f) amino acid residues 234, 310, 316, 484 and 493 (Epitope F); and g) amino acid residues 327 and 404 (Epitope Fs), wherein amino acid residue numbering of (a)-(g) is based on the amino acid sequence of any of SEQ ID NOs:4-13; and h) amino acid residues 391, 393, 394 and 395 (Epitope D); i) amino acid residues 406, 411 and 412 (Epitope E); j) amino acid residues 234, 310, 316, 483 and 492 (Epitope F); and k) amino acid residues 327 and 403 (Epitope Fs), wherein amino acid residue numbering of (h)-(k) is based on the amino acid sequence of SEQ ID NOs:1-3, from two or more norovirus strains that are different from one another, wherein the synthetic backbone molecule allows for formation of two or more norovirus conformational epitopes, and wherein the synthetic backbone molecule is not a norovirus capsid protein.

Additionally provided herein is a synthetic backbone molecule comprising a set of amino acid residues that form a norovirus conformational epitope, wherein the set of amino acid residues consist of amino acid residues 234, 310, 316, 484 and 493 (Epitope F), wherein amino acid residue numbering is based on the amino acid sequence of any of SEQ ID NOs:4-13 or amino acid residues 234, 310, 316, 483 and 492 (Epitope F), wherein amino acid residue numbering is based on the amino acid sequence of SEQ ID NOs:1-3, wherein the synthetic backbone molecule is not a norovirus capsid protein.

Also provided herein is a norovirus P particle consisting of multiple copies of a norovirus P domain backbone from norovirus strain GII.4.1974 (SEQ ID NO:1), norovirus strain GII.4.1987 (SEQ ID NO:2), norovirus strain GII.4.1997 (SEQ ID NO:3), norovirus strain GII.4.2002 (SEQ ID NO:4), norovirus strain GII.4.2002a (SEQ ID NO:5), norovirus strain GII.4.2004 (SEQ ID NO:6), norovirus strain GII.4.2005 (SEQ ID NO:7), norovirus strain GII.4.2006 (SEQ ID NO:8), norovirus strain GII.4.2007 (SEQ ID NO:9), norovirus strain GII.4.2008a (SEQ ID NO:10), norovirus strain GII.4.2008s (SEQ ID NO:11), norovirus strain GII.4.2009 (SEQ ID NO:12), or norovirus strain GII.4.2012 (SEQ ID NO:13) in which two or more, in any combination, of the following sets of amino acid residues (a)-(k): a) amino acid residues 294, 296, 297, 298, 368 and 372 (Epitope A); b) amino acid residues 333 and 382 (Epitope B); c) amino acid residues 340 and 376 (Epitope C); d) amino acid residues 391, 393, 394, 395 and 396 (Epitope D); e) amino acid residues 407, 412 and 413 (Epitope E); f) amino acid residues 234, 310, 316, 484 and 493 (Epitope F); and g) amino acid residues 327 and 404 (Epitope Fs), wherein amino acid residue numbering of (a)-(g) is based on the amino acid sequence of any of SEQ ID NOs:4-13; and h) amino acid residues 391, 393, 394 and 395 (Epitope D); i) amino acid residues 406, 411 and 412 (Epitope E); j) amino acid residues 234, 310, 316, 483 and 492 (Epitope F); k) amino acid residues 327 and 403 (Epitope Fs), wherein amino acid residue numbering of (h)-(k) is based on the amino acid sequence of SEQ ID NOs:1-3, are substituted into the P domain backbone to introduce at least one epitope from each of two or more norovirus strains of the above norovirus strains, each of which is different from one another and each of which is different from the norovirus strain of the P domain backbone, wherein the epitopes are presented on the P particle surface.

In a further embodiment, the present invention provides a norovirus P particle comprising a set of amino acid residues that form a norovirus conformational epitope, wherein the set of amino acid residues consist of amino acid residues 234, 310, 316, 484 and 493 (Epitope F), wherein amino acid residue numbering is based on the amino acid sequence of any of SEQ ID NOs:4-13 or amino acid residues 234, 310, 316, 483 and 492 (Epitope F), wherein amino acid residue numbering is based on the amino acid sequence of SEQ ID NOs:1-3, wherein the synthetic backbone molecule is not a norovirus capsid protein. The present invention further provides therapeutic methods. Thus, in one embodiment, the present invention provides a method of producing an immune response to a norovirus in a subject, comprising administering to the subject an effective amount of the chimeric norovirus capsid protein of this invention, the synthetic backbone molecule of this invention, the P particle of this invention, the mimitope of this invention, the nucleic acid molecule of this invention, the vector of this invention, the VRP of this invention, the VLP of this invention and/or the composition of this invention.

Additionally provided herein is a chimeric norovirus capsid protein consisting of a norovirus VP1 major capsid protein backbone from norovirus strain GII.3 (SEQ ID NO:14), in which one or more, in any combination, of the following sets of amino acid residues (a)-(k) are substituted into the norovirus capsid protein backbone from norovirus strain GII.3 to introduce one or more epitope in any combination, from one or more different norovirus strains having an amino acid sequence of SEQ ID Nos: 1, 2, 3, 4, 5, 6, 7, 8, 9, 10, 11, 12, or 13, in any combination, as follows: a) amino acid residues 294, 296, 297, 298, 368 and 372 (Epitope A) substituted at positions 294, 310, 311, 312, 381 and 384, respectively, in the amino acid sequence of SEQ ID NO:14; b) amino acid residues 333 and 382 (Epitope B) substituted at positions 347 and 394, respectively, in the amino acid sequence of SEQ ID NO:14; c) amino acid residues 340 and 376 (Epitope C) substituted at positions 353 and 388, respectively, in the amino acid sequence of SEQ ID NO:14; d) amino acid residues 391, 393, 394 and 395 (Epitope D) substituted at positions 403, 404, 405 and 406, respectively, in the amino acid sequence of SEQ ID NO:14; e) amino acid residues 407, 412 and 413 (Epitope E) substituted at positions 415, 420 and 421, respectively, in the amino acid sequence of SEQ ID NO:14; f) amino acid residues 234, 310, 316, 484 and 493 (Epitope F) substituted at positions 234, 324, 330, 492 and 501, respectively, in the amino acid sequence of SEQ ID NO:14; and g) amino acid residues 327 and 404 (Epitope Fs) substituted at positions 341 and 412, respectively, in the amino acid sequence of SEQ ID NO:14, wherein amino acid residue numbering of (a)-(g) is based on the amino acid sequence of any of SEQ ID NOs:4-13; and h) amino acid residues 391, 393, 394 and 395 (Epitope D) substituted at positions 403, 404, 405 and 406, respectively, in the amino acid sequence of SEQ ID NO:14; i) amino acid residues 406, 411 and 412 (Epitope E) substituted at positions 415, 420 and 421, respectively, in the amino acid sequence of SEQ ID NO:14; j) amino acid residues 234, 310, 316, 483 and 492 (Epitope F) substituted at positions 234, 324, 330, 492 and 501, respectively, in the amino acid sequence of SEQ ID NO:14, and k) amino acid residues 327 and 403 (Epitope Fs) substituted at positions 341 and 412, respectively, in the amino acid sequence of SEQ ID NO:14, wherein amino acid residue numbering of (h)-(k) is based on the amino acid sequence of SEQ ID NOs:1-3.

Further provided herein is a norovirus P particle consisting of multiple copies of a norovirus P domain backbone from norovirus strain GII.3 (SEQ ID NO:14), in which one or more, in any combination, of the following sets of amino acid residues (a)-(k) are substituted into the norovirus P domain backbone from norovirus strain GII.3 to introduce one or more epitope in any combination, from one or more different norovirus strains having an amino acid sequence of SEQ ID Nos:1, 2, 3, 4, 5, 6, 7, 8, 9, 10, 11, 12, or 13, in any combination, as follows: a) amino acid residues 294, 296, 297, 298, 368 and 372 (Epitope A) substituted at positions 294, 310, 311, 312, 381 and 384, respectively, in the amino acid sequence of SEQ ID NO:14; b) amino acid residues 333 and 382 (Epitope B) substituted at positions 347 and 394, respectively, in the amino acid sequence of SEQ ID NO:14; c) amino acid residues 340 and 376 (Epitope C) substituted at positions 353 and 388, respectively, in the amino acid sequence of SEQ ID NO:14; d) amino acid residues 391, 393, 394, and 395 (Epitope D) substituted at positions 403, 404, 405 and 406, respectively, in the amino acid sequence of SEQ ID NO:14; e) amino acid residues 407, 412 and 413 (Epitope E) substituted at positions 415, 420 and 421, respectively, in the amino acid sequence of SEQ ID NO:14; f) amino acid residues 234, 310, 316, 484 and 493 (Epitope F) substituted at positions 234, 324, 330, 492 and 501, respectively, in the amino acid sequence of SEQ ID NO:14; and g) amino acid residues 327 and 404 (Epitope Fs) substituted at positions 341 and 412, respectively, in the amino acid sequence of SEQ ID NO:14, wherein amino acid residue numbering of (a)-(g) is based on the amino acid sequence of any of SEQ ID NOs:4-13; and h) amino acid residues 391, 393, 394 and 395 (Epitope D) substituted at positions 403, 404, 405 and 406, respectively, in the amino acid sequence of SEQ ID NO:14; i) amino acid residues 406, 411 and 412 (Epitope E) substituted at positions 415, 420 and 421, respectively, in the amino acid sequence of SEQ ID NO:14; j) amino acid residues 234, 310, 316, 483 and 492 (Epitope F) substituted at positions 234, 324, 330, 492 and 501, respectively, in the amino acid sequence of SEQ ID NO:14, and k) amino acid residues 327 and 403 (Epitope Fs) substituted at positions 341 and 412, respectively, in the amino acid sequence of SEQ ID NO:14, wherein amino acid residue numbering of (h)-(k) is based on the amino acid sequence of SEQ ID NOs:1-3, wherein the epitopes are presented on the P particle surface.

Also provided herein is a vaccinating a subject to produce an immune response against norovirus, comprising administering to the subject an effective amount of the chimeric norovirus capsid protein of this invention, the synthetic backbone molecule of this invention, the P particle of this invention, the mimitope of this invention, the nucleic acid molecule of this invention, the vector of this invention, the VRP of this invention, the VLP of this invention and/or the composition of this invention.

Also provided herein is a method of treating a norovirus infection in a subject in need thereof, comprising administering to the subject an effective amount of the chimeric norovirus capsid protein of this invention, the synthetic backbone molecule of this invention, the P particle of this invention, the mimitope of this invention, the nucleic acid molecule of this invention, the vector of this invention, the VRP of this invention, the VLP of this invention and/or the composition of this invention.

Further provided herein is a method of preventing a disorder associated with a norovirus infection in a subject, comprising administering to the subject an effective amount of the chimeric norovirus capsid protein of this invention, the synthetic backbone molecule of this invention, the P particle of this invention, the mimitope of this invention, the nucleic acid molecule of this invention, the vector of this invention, the VRP of this invention, the VLP of this invention and/or the composition of this invention.

In additional embodiments, the present invention provides a method of protecting a subject from the effects of norovirus infection, comprising administering to the subject an effective amount of the chimeric norovirus capsid protein of this invention, the synthetic backbone molecule of this invention, the P particle of this invention, the mimitope of this invention, the nucleic acid molecule of this invention, the vector of this invention, the VRP of this invention, the VLP of this invention and/or the composition of this invention.

The present invention also provides diagnostic methods. Thus, in one aspect, the present invention provides a method of detecting a neutralizing antibody to a norovirus, the method comprising determining whether an antibody binds to the chimeric norovirus capsid protein of this invention, the synthetic backbone molecule of this invention, the P particle of this invention, the mimitope of this invention, the VRP of this invention and/or the VLP of this invention, wherein binding by the antibody to the chimeric norovirus capsid protein of this invention, the synthetic backbone molecule of this invention, the P particle of this invention, the mimitope of this invention, the VRP of this invention and/or the VLP of this invention indicates that the antibody is a neutralizing antibody to a norovirus.

A method is also provided herein of identifying a neutralizing antibody to a norovirus, comprising: (a) contacting an antibody with the chimeric norovirus capsid protein of this invention, the synthetic backbone molecule of this invention, the P particle of this invention, the mimitope of this invention, the VRP of this invention and/or the VLP of this invention; and (b) determining if the antibody binds to the chimeric norovirus capsid protein of this invention, the synthetic backbone molecule of this invention, the P particle of this invention, the mimitope of this invention, the VRP of this invention and/or the VLP of this invention, wherein binding by the antibody to the chimeric norovirus capsid protein of this invention, the synthetic backbone molecule of this invention, the P particle of this invention, the mimitope of this invention, the VRP of this invention and/or the VLP of this invention identifies the antibody as a neutralizing antibody to a norovirus.

In further embodiments, the present invention provides a method of identifying an immunogenic composition that induces a neutralizing antibody to a norovirus in a subject, the method comprising: (a) contacting a biological sample from a subject that has been administered the immunogenic composition with the chimeric norovirus capsid protein of this invention, the synthetic backbone molecule of this invention, the P particle of this invention, the mimitope of this invention, the VRP of this invention and/or the VLP of this invention; (b) determining if the biological sample comprises an antibody that binds the chimeric norovirus capsid protein of this invention, the synthetic backbone molecule of this invention, the P particle of this invention, the mimitope of this invention, the VRP of this invention and/or the VLP of this invention; and (c) identifying the immunogenic composition as inducing a neutralizing antibody to a norovirus in the subject if the biological sample comprises an antibody that binds to the chimeric norovirus capsid protein of this invention, the synthetic backbone molecule of this invention, the P particle of this invention, the mimitope of this invention, the VRP of this invention and/or the VLP of this invention.

Also provided herein is a method of identifying an immunogenic composition that induces a neutralizing antibody to a norovirus in a subject, the method comprising: (a) administering an immunogenic composition comprising a norovirus antigen to a subject in an amount effective to induce antibodies against the norovirus antigen; (b) contacting a biological sample from the subject with the chimeric norovirus capsid protein of this invention, the synthetic backbone molecule of this invention, the P particle of this invention, the mimitope of this invention, the VRP of this invention and/or the VLP of this invention; (c) determining if the biological sample comprises an antibody that binds the chimeric norovirus capsid protein of this invention, the synthetic backbone molecule of this invention, the P particle of this invention, the mimitope of this invention, the VRP of this invention and/or the VLP of this invention; and (d) identifying the immunogenic composition as inducing a neutralizing antibody to a norovirus in the subject if the biological sample comprises an antibody that binds the chimeric norovirus capsid protein of this invention, the synthetic backbone molecule of this invention, the P particle of this invention, the mimitope of this invention, the VRP of this invention and/or the VLP of this invention.

BRIEF DESCRIPTION OF THE DRAWINGS

Figure 1:
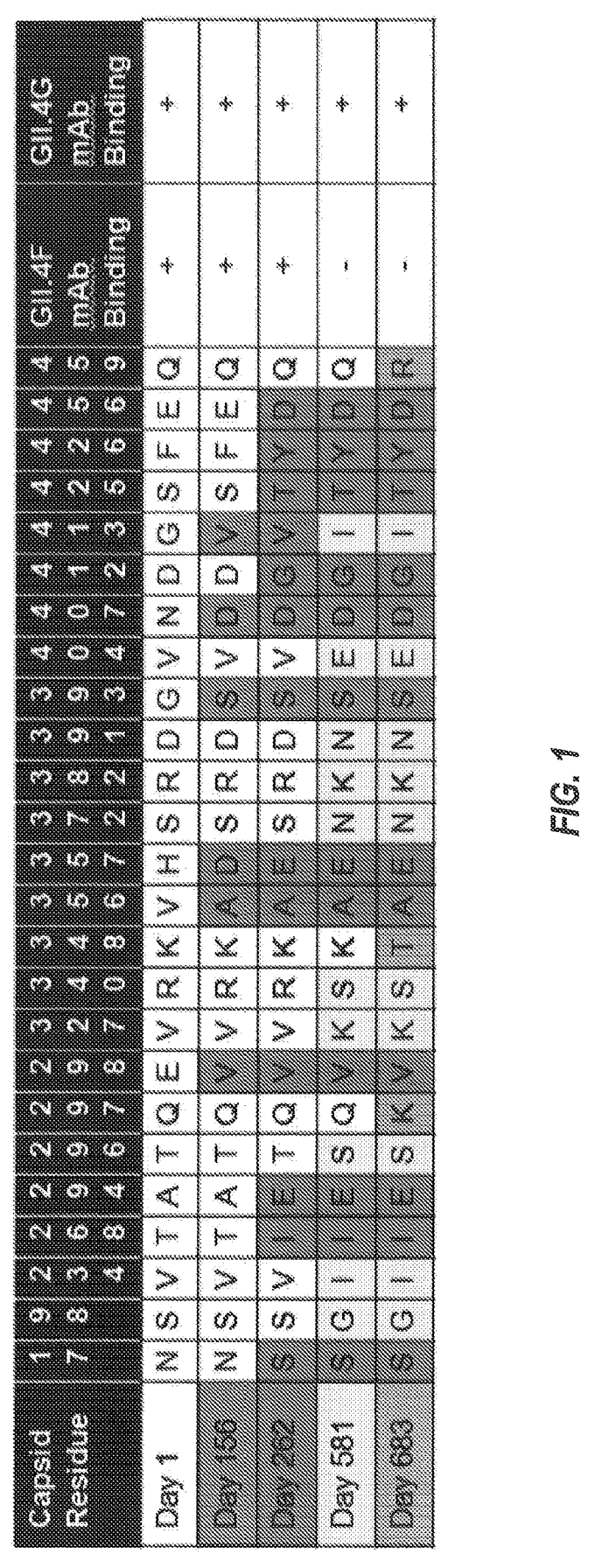

FIG. 1: Long-term in vivo evolution results in loss of GII.4 Epitope F, a conserved GII.4 blockade antibody epitope. Virus-like particles representing norovirus sequences isolated from an immunocompromised transplant patient over a 683-day period were evaluated for binding to mAbs GII.4F and GII.4G by enzyme immunoassay. Both mAbs recognize conserved GII.4 blockade epitopes that overlap each other and are occluded by structural conformation. After a minimum of 581 days of in vivo evolution, capsid sequence changes resulted in loss of binding of human mAb GII.4F but not mouse mAb GII.4G.

FIG. 2: Residues 327 and 404 are key binding sites for GII.4F mAb. To map the epitope for the GII.4F mAb, amino acid changes in the capsid protein between Day 1 and Day 581 strains were compared and sets of changes introduced into the 581 backbone sequence. Chimeric VLPs were evaluated for mAb binding by EIA and $EC_{50}$ titers determined. Exchanged residues are shaded to indicate gain or loss of GII.4F mAb binding (see FIGS. 9A-B). Exchange of valine into residues 327 and 404 gained binding of GII.4F mAb to 581 (581.F) and while replacement of valine at 327 and 404 in GII.4.2002 (2002.581F) lost binding of the GII.4F mAb.

FIG. 3: Homology models of Epitope F interactions between Days 262 (left) and 581 (right) viruses. Amino acid positions 327, 401, and 404 are shown. Three hydrogen bonds (dashed lines) are evident among residues 327V, 401Q, and 404V in the Day 262 model, while two additional hydrogen bonds (dashed lines) are formed in the Day 581 model among 327K, 401Q, and 404E.

FIG. 4: GII.4F antibody access to Epitope F is influenced by residue 234, a residue outside of the epitope. GII.4F mAb $EC_{50}$ titer is mediated by both the number of binding sites available ($B_{max}$) and the affinity of the antibody for the epitope. To distinguish the effects of the five residues comprising 581.FX, chimeric VLPs containing admixtures of residues were tested for GII.4F mAb binding by EIA and $B_{max}$ and $K_D$ values calculated. Changes in residues 340 and 391 did not change GII.4F mAb binding or access. The $K_D$ for the epitope was consistent between the VLPs with valine at positions 327 and 404, identifying these residues as part of the GII.4 Epitope F. In comparison, 234V did not associate with changes in $K_D$. The 234V VLPs had higher $B_{max}$ compared to 581.F, indicating that 234 may be influencing GII.4F mAb binding via long-range allosteric effects, as described for the NERK motif. Bold values are significantly different from 581.F. <LOD, less than the limit of detection.

FIG. 5: Residues important for mediating GII.4 norovirus antigenicity. A homology model of a P2 domain dimer of GII.4.2006a bound to A antigen with identified blockade antibody Epitopes A, D, E, and F and the "breathing core" residues (NERK plus 234) that mediate global particle conformation.

FIGS. 6A-6C: GII.4E mAb binding is regulated by global particle conformation and surrounding local topology. (FIG. 6A) GII.4.2002 VLP binding to ligand was blocked by GII.4E at either room temperature (RT) (black) or 37° C. (red) and mean percent control binding compared to no Ab was fit with sigmoidal dose response curve analysis with Hill slope and $EC_{50}$ values calculated. Elevated temperature of incubation resulted in a steeper curve and lower $EC_{50}$ titer, indicating antibody access to Epitope E is dependent upon particle conformation, as described for Epitopes F and G. (FIG. 6B) Exchange of both Epitope E and F residues into the 581 backbone (581.2002E/F) improved binding of GII.4E mAb compared to exchanging only either Epitope E (581.2002E) or Epitope F (581.F) residues. *Significantly different from 581.2002E/F. (FIG. 6C) To distinguish the effects of Epitope E and F residues on GII.4E binding, chimeric VLPs were tested for GII.4E binding by EIA and Bmax and $K_D$ values calculated. Exchange of Day 581 Epitope F residues into the 2002 backbone (2002.581F) did not change the $K_D$ for GII.4E but did decrease the Bmax, indicating that Epitope F residues mediate GII.4E epitope access. In support of this hypothesis, exchange of both Epitope E and F residues from 2002 into 581 (581.2002E/F) was necessary to restore GII.4E binding. Bold values are significantly different from GII.4.2002. <LOD: less than the limit of detection. Shading indicates residues involved in GII.4E epitope binding and access to the epitope.

Figure 7:
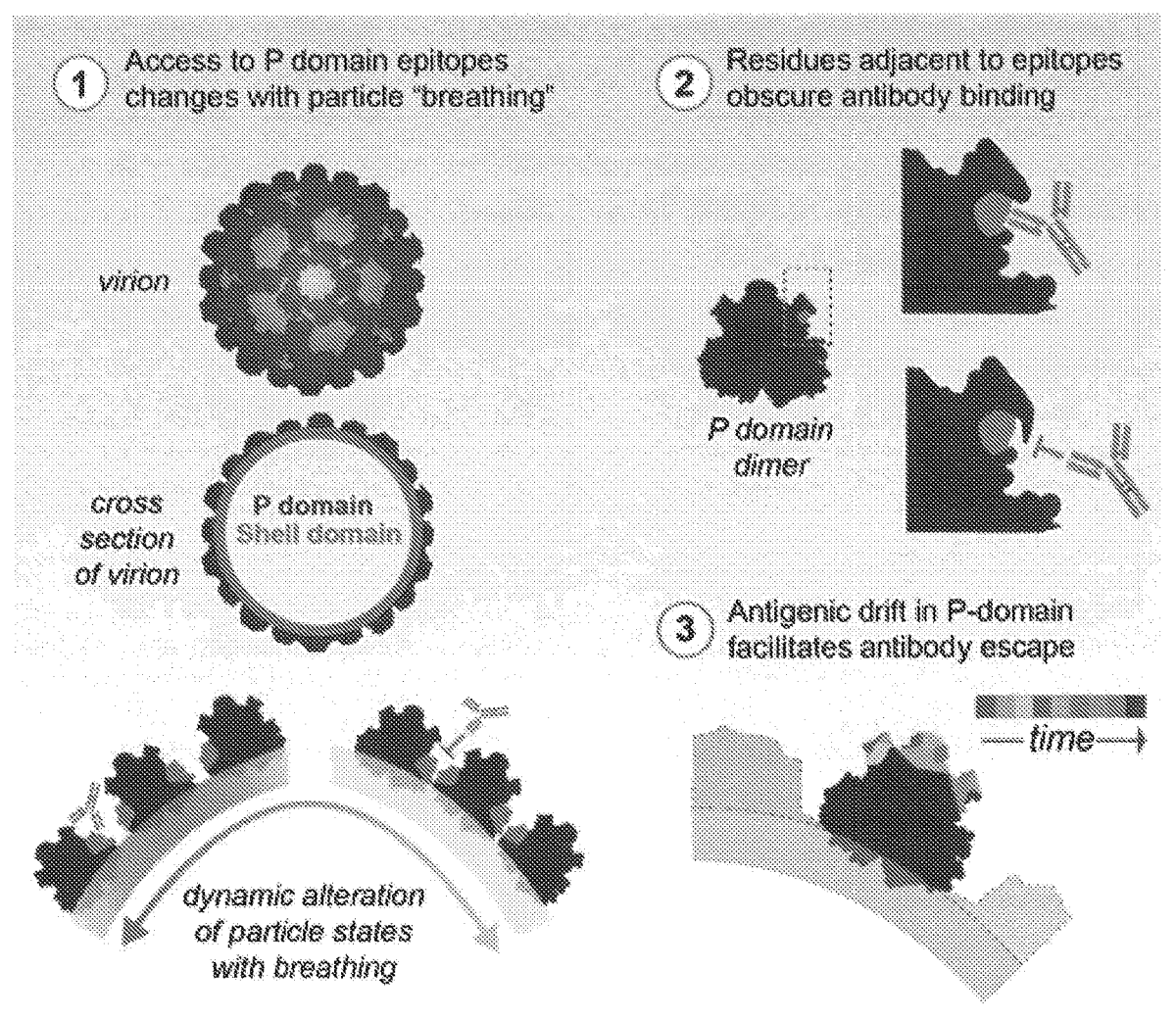

FIG. 7: Sequence and spatial flexibility within the capsid of GII.4 noroviruses mitigates antibody-mediated protective immunity. Three mechanisms of immune evasion are proposed here. First, antibody binding to epitopes can be occluded by steric hindrance resulting from particle contraction during "breathing" (Epitopes E, F, and G). Second, antibody binding to epitopes can be occluded by steric hindrance resulting from local particle conformation (Epitopes E and F). Third, antigenic drift in highly antigenic, surface exposed epitopes (Epitopes A, D, and E).

(FIG. 9A) Chimeric VLPs composed of either all of the residue changes between Day 1 and Day 581 (581.Day1) or subsets of residues that changed between Day 1 and Day 581 (581.F1-F4). Residue changes in F2-F4 restored GII.4F EC50<0.2 µg/ml. (FIG. 9B) The five residue subset 234, 327, 340, 391, and 404 (581.FX) gained GII.4F binding. Only VLPs with admixtures of valine at residues 327 and 404 retained binding to GII.4F. Dashed line marks the limit of detection. Error bars represent 95% confidence intervals. *Significantly different from 581.Day1 or 581.FX.

FIGS. 10A-10B: Epitopes of various human norovirus (NoV) strains. Numbering of amino acids is based on amino acid position of the full amino acid sequence of the norovirus strains listed as provided in the GenBank® Database or as provided herein (FIGS. 10A-10B). Epitope F can also include residue 234.

FIG. 12: Blockade monoclonal antibodies to epitope D (NVB 97 and NO66) anchor at residues 393 and 396 of the protruding loop of epitope D. Half maximum binding titers with 95% confidence intervals (95% CI) were determined for monoclonal antibodies NVB 97, NO66, and non-epitope D antibody N0224 to VLPs with substitutions reflective of natural variation between pandemic strains GII.4 2009 and 2012 within epitope D at residues 393 and 396. Bold numbers are significantly different from GII.4 2009.

DETAILED DESCRIPTION OF THE INVENTION

Figure 6A:
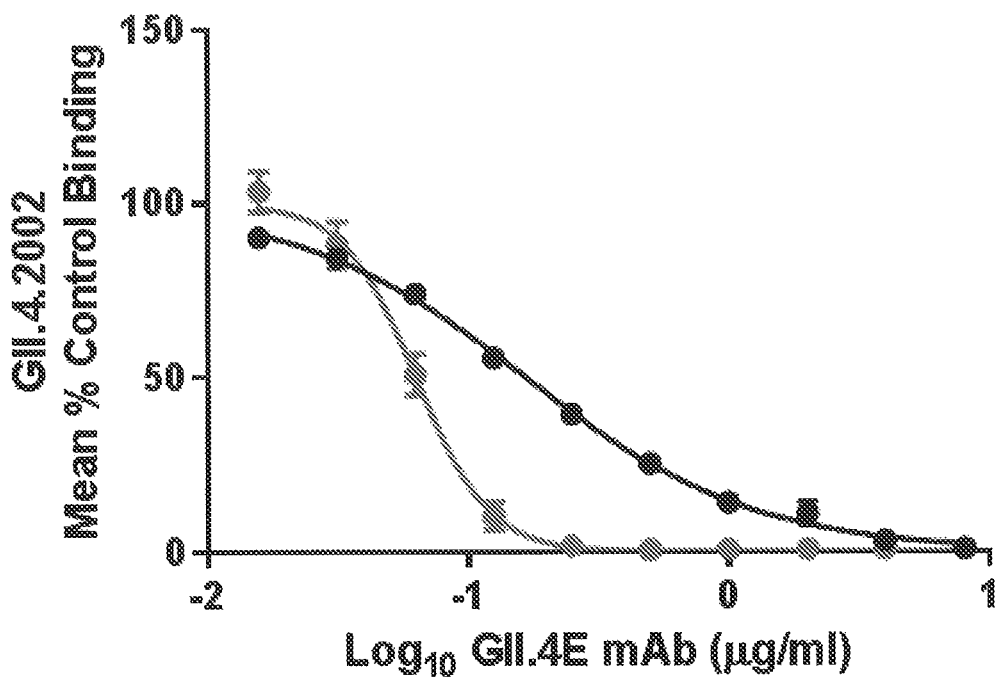

The present invention will now be described more fully hereinafter with reference to the accompanying drawings and specification, in which preferred embodiments of the invention are shown. This invention may, however, be embodied in different forms and should not be construed as limited to the embodiments set forth herein.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

In one embodiment, the present invention provides a chimeric norovirus capsid protein consisting of a norovirus VP1 major capsid protein backbone from norovirus strain GII.4.1974 (SEQ ID NO:1), norovirus strain GII.4.1987 (SEQ ID NO:2), norovirus strain GII.4.1997 (SEQ ID NO:3), norovirus strain GII.4.2002 (SEQ ID NO:4), norovirus strain GII.4.2002a (SEQ ID NO:5), norovirus strain GII.4.2004 (SEQ ID NO:6), norovirus strain GII.4.2005 (SEQ ID NO:7), norovirus strain GII.4.2006 (SEQ ID NO:8), norovirus strain GII.4.2007 (SEQ ID NO:9), norovirus strain GII.4.2008a (SEQ ID NO:10), norovirus strain GII.4.2008s (SEQ ID NO:11), norovirus strain GII.4.2009 (SEQ ID NO:12), or norovirus strain GII.4.2012 (SEQ ID NO:13) in which two or more (e.g., 2, 3, 4, 5, 6, 7, 8, 9, 10, 11, etc.), in any combination, of the following sets of amino acid residues (a)-(k): a) amino acid residues 294, 296, 297, 298, 368 and 372 (Epitope A); b) amino acid residues 333 and 382 (Epitope B); c) amino acid residues 340 and 376 (Epitope C); d) amino acid residues 391, 393, 394, 395 and 396 (Epitope D); e) amino acid residues 407, 412 and 413 (Epitope E); f) amino acid residues 234, 310, 316, 484 and 493 (Epitope F); and g) amino acid residues 327 and 404 (Epitope Fs), wherein amino acid residue numbering of (a)-(g) is based on the amino acid sequence of any of SEQ ID NOs:4-13; and h) amino acid residues 391, 393, 394 and 395 (Epitope D); i) amino acid residues 406, 411 and 412 (Epitope E); j) amino acid residues 234, 310, 316, 483 and 492 (Epitope F), and k) amino acid residues 327 and 403 (Epitope Fs), wherein amino acid residue numbering of (h)-(k) is based on the amino acid sequence of SEQ ID NOs:1-3, are substituted into the capsid protein backbone to introduce at least one epitope from each of two or more (e.g., 2, 3, 4, 5, 6, 7, 8, 9, 10, 11, 12, 13) different norovirus strains of the above norovirus strains, each of which is different from one another and each of which is different from the norovirus strain of the capsid protein backbone.

In another embodiment, the present invention provides a chimeric norovirus capsid protein consisting of a norovirus VP1 major capsid protein backbone from norovirus strain GII.4.1974 (SEQ ID NO:1), norovirus strain GII.4.1987 (SEQ ID NO:2), norovirus strain GII.4.1997 (SEQ ID NO:3), norovirus strain GII.4.2002 (SEQ ID NO:4), norovirus strain GII.4.2002a (SEQ ID NO:5), norovirus strain GII.4.2004 (SEQ ID NO:6), norovirus strain GII.4.2005 (SEQ ID NO:7), norovirus strain GII.4.2006 (SEQ ID NO:8), norovirus strain GII.4.2007 (SEQ ID NO:9), norovirus strain GII.4.2008a (SEQ ID NO:10), norovirus strain GII.4.2008s (SEQ ID NO:11), norovirus strain GII.4.2009 (SEQ ID NO:12), or norovirus strain GII.4.2012 (SEQ ID NO:13) in which amino acid residues 234, 310, 316, 484 and 493 (Epitope F), wherein amino acid residue numbering is based on the amino acid sequence of any of SEQ ID NOs:4-13 or amino acid residues 234, 310, 316, 483 and 492 (Epitope F), wherein amino acid residue numbering is based on the amino acid sequence of any of SEQ ID NOs:1-3, are substituted into the capsid protein backbone to introduce Epitope F from a norovirus strain that is different from the norovirus strain of the capsid protein backbone.

In some embodiments, the chimeric norovirus capsid protein described above can be a capsid protein in which, in addition to the incorporation of a heterologous Epitope F, one or more of the following sets of amino acid residues (a)-(i): a) amino acid residues 294, 296, 297, 298, 368 and 372 (Epitope A); b) amino acid residues 333 and 382 (Epitope B); c) amino acid residues 340 and 376 (Epitope C); d) amino acid residues 391, 393, 394, 395 and 396 (Epitope D); e) amino acid residues 407, 412 and 413 (Epitope E); and f) amino acid residues 327 and 404 (Epitope Fs), wherein amino acid residue numbering of (a)-(f) is based on the amino acid sequence of any of SEQ ID NOs:4-13, and g) amino acid residues 391, 393, 394 and 395 (Epitope D); h) amino acid residues 406, 411 and 412 (Epitope E); and i) amino acid residues 327 and 403 (Epitope Fs), wherein amino acid residue numbering of (g)-(i) is based on the amino acid sequence of SEQ ID NOs:1-3, are substituted into the capsid protein backbone to introduce at least one epitope from a norovirus strain that is different from the norovirus strain of Epitope F and different from the strain of the capsid protein backbone.

In a further embodiment, the present invention provides a synthetic backbone molecule comprising two or more sets of amino acid residues wherein each set of amino acid residues forms a norovirus conformational epitope, wherein the two or more sets of amino acid residues each form a conformational epitope from two or more norovirus strains that are different from one another and wherein the two or more sets of amino acid residues are selected in any combination from the group consisting of the following sets of amino acid residues (a)-(k): a) amino acid residues 294, 296, 297, 298, 368 and 372 (Epitope A); b) amino acid residues 333 and 382 (Epitope B); c) amino acid residues 340 and 376 (Epitope C); d) amino acid residues 391, 393, 394, 395 and 396 (Epitope D); e) amino acid residues 407, 412 and 413 (Epitope E); f) amino acid residues 234, 310, 316, 484 and 493 (Epitope F); and g) amino acid residues 327 and 404 (Epitope Fs), wherein amino acid residue numbering of (a)-(g) is based on the amino acid sequence of any of SEQ ID NOs:4-13; and h) amino acid residues 391, 393, 394 and 395 (Epitope D); i) amino acid residues 406, 411 and 412 (Epitope E); j) amino acid residues 234, 310, 316, 483 and 492 (Epitope F); and k) amino acid residues 327 and 403 (Epitope Fs), wherein amino acid residue numbering of (h)-(k) is based on the amino acid sequence of SEQ ID NOs:1-3, from two or more norovirus strains that are different from one another, wherein the synthetic backbone molecule allows for formation of two or more norovirus conformational epitopes, and wherein the synthetic backbone molecule is not a norovirus capsid protein.

Additionally provided herein is a synthetic backbone molecule comprising a set of amino acid residues that form a norovirus conformational epitope, wherein the set of amino acid residues consist of amino acid residues 234, 310, 316, 484 and 493 (Epitope F), wherein amino acid residue numbering is based on the amino acid sequence of any of SEQ ID NOs:4-13 or amino acid residues 234, 310, 316, 483 and 492 (Epitope F), wherein amino acid residue numbering is based on the amino acid sequence of SEQ ID NOs:1-3, wherein the synthetic backbone molecule is not a norovirus capsid protein.

In some embodiments, the synthetic backbone molecule described above can be a synthetic backbone molecule in which, in addition to Epitope F, one or more of the following sets of amino acid residues (a)-(i): a) amino acid residues 294, 296, 297, 298, 368 and 372 (Epitope A); b) amino acid residues 333 and 382 (Epitope B); c) amino acid residues 340 and 376 (Epitope C); d) amino acid residues 393, 394 and 395 (Epitope D); e) amino acid residues 407, 412 and 413 (Epitope E); and f) amino acid residues 327 and 404 (Epitope Fs), wherein amino acid residue numbering of (a)-(f) is based on the amino acid sequence of any of SEQ ID NOs:4-13, and g) amino acid residues 391, 393, 394 and 395 (Epitope D); h) amino acid residues 406, 411 and 412 (Epitope E); and i) amino acid residues 327 and 403 (Epitope Fs), wherein amino acid residue numbering of (g)-(i) is based on the amino acid sequence of SEQ ID NOs:1-3, are present in the synthetic backbone molecule to introduce at least one epitope from a norovirus strain that is different from the norovirus strain of Epitope F.

Also provided herein is a norovirus P particle consisting of multiple copies of a norovirus P domain backbone from norovirus strain GII.4.1974 (SEQ ID NO:1), norovirus strain GII.4.1987 (SEQ ID NO:2), norovirus strain GII.4.1997 (SEQ ID NO:3), norovirus strain GII.4.2002 (SEQ ID NO:4), norovirus strain GII.4.2002a (SEQ ID NO:5), norovirus strain GII.4.2004 (SEQ ID NO:6), norovirus strain GII.4.2005 (SEQ ID NO:7), norovirus strain GII.4.2006 (SEQ ID NO:8), norovirus strain GII.4.2007 (SEQ ID NO:9), norovirus strain GII.4.2008a (SEQ ID NO:10), norovirus strain GII.4.2008s (SEQ ID NO:11), norovirus strain GII.4.2009 (SEQ ID NO:12), or norovirus strain GII.4.2012 (SEQ ID NO:13) in which two or more, in any combination, of the following sets of amino acid residues (a)-(k): a) amino acid residues 294, 296, 297, 298, 368 and 372 (Epitope A); b) amino acid residues 333 and 382 (Epitope B); c) amino acid residues 340 and 376 (Epitope C); d) amino acid residues 391, 393, 394, 395 and 396 (Epitope D); e) amino acid residues 407, 412 and 413 (Epitope E); f) amino acid residues 234, 310, 316, 484 and 493 (Epitope F); and g) amino acid residues 327 and 404 (Epitope Fs), wherein amino acid residue numbering of (a)-(g) is based on the amino acid sequence of any of SEQ ID NOs:4-13; and h) amino acid residues 391, 393, 394 and 395 (Epitope D); i) amino acid residues 406, 411 and 412 (Epitope E); j) amino acid residues 234, 310, 316, 483 and 492 (Epitope F); k) amino acid residues 327 and 403 (Epitope Fs), wherein amino acid residue numbering of (h)-(k) is based on the amino acid sequence of SEQ ID NOs:1-3, are substituted into the P domain backbone to introduce at least one epitope from each of two or more norovirus strains of the above norovirus strains, each of which is different from one another and each of which is different from the norovirus strain of the P domain backbone, wherein the epitopes are presented on the P particle surface.

In a further embodiment, the present invention provides a norovirus P particle comprising a set of amino acid residues that form a norovirus conformational epitope, wherein the set of amino acid residues consist of amino acid residues 234, 310, 316, 484 and 493 (Epitope F), wherein amino acid residue numbering is based on the amino acid sequence of any of SEQ ID NOs:4-13 or amino acid residues 234, 310, 316, 483 and 492 (Epitope F), wherein amino acid residue numbering is based on the amino acid sequence of SEQ ID NOs:1-3, wherein the synthetic backbone molecule is not a norovirus capsid protein.

In further embodiments, the norovirus P particle of described above can be a norovirus P particle in which, in addition to Epitope F, one or more of the following sets of amino acid residues (a)-(i): a) amino acid residues 294, 296, 297, 298, 368 and 372 (Epitope A); b) amino acid residues 333 and 382 (Epitope B); c) amino acid residues 340 and 376 (Epitope C); d) amino acid residues 391, 393, 394, 395 and 396 (Epitope D); e) amino acid residues 407, 412 and 413 (Epitope E); and f) amino acid residues 327 and 404

(Epitope Fs), wherein amino acid residue numbering of (a)-(f) is based on the amino acid sequence of any of SEQ ID NOs:4-13, and g) amino acid residues 391, 393, 394 and 395 (Epitope D); h) amino acid residues 406, 411 and 412 (Epitope E); and i) amino acid residues 327 and 403 (Epitope Fs); and wherein amino acid residue numbering of (g)-(i) is based on the amino acid sequence of SEQ ID NOs:1-3, are present in the norovirus P particle to introduce at least one epitope from a norovirus strain that is different from the norovirus strain of Epitope F.

Additionally provided herein is a chimeric norovirus capsid protein consisting of a norovirus VP1 major capsid protein backbone from norovirus strain GII.3 (SEQ ID NO:14), in which one or more (e.g., 2, 3, 4, 5, 6, 7, 8, 9, 10, etc.), in any combination, of the following sets of amino acid residues (a)-(k) are substituted into the norovirus capsid protein backbone from norovirus strain GII.3 to introduce one or more (e.g., 2, 3, 4, 5, 6, 7, 8, 9, 10, etc.) epitope in any combination, from one or more (e.g., 2, 3, 4, 5, 6, 7, 8, 9, 10, 11, 12, 13, etc.) different norovirus strains having an amino acid sequence of SEQ ID Nos:1, 2, 3, 4, 5, 6, 7, 8, 9, 10, 11, 12, or 13, in any combination, as follows: a) amino acid residues 294, 296, 297, 298, 368 and 372 (Epitope A) are substituted at positions 294, 310, 311, 312, 381 and 384, respectively, in the amino acid sequence of SEQ ID NO:14 (which are the corresponding residue sites in the amino acid sequence of the capsid protein of GII.3); b) amino acid residues 333 and 382 (Epitope B) substituted at positions 347 and 394, respectively, in the amino acid sequence of SEQ ID NO:14; c) amino acid residues 340 and 376 (Epitope C) substituted at positions 353 and 388, respectively, in the amino acid sequence of SEQ ID NO:14; d) amino acid residues 391, 393, 394 and 395 (Epitope D) substituted at positions 403, 404, 405 and 406, respectively, in the amino acid sequence of SEQ ID NO:14; e) amino acid residues 407, 412 and 413 (Epitope E) substituted at positions 415, 420 and 421, respectively, in the amino acid sequence of SEQ ID NO:14; amino acid residues 234, 310, 316, 484 and 493 (Epitope F) substituted at positions 234, 324, 330, 492 and 501, respectively, in the amino acid sequence of SEQ ID NO:14; and g) amino acid residues 327 and 404 (Epitope Fs) substituted at positions 341 and 412, respectively, in the amino acid sequence of SEQ ID NO:14, wherein amino acid residue numbering of (a)-(g) is based on the amino acid sequence of any of SEQ ID NOs:4-13; and h) amino acid residues 391, 393, 394 and 395 (Epitope D) substituted at positions 403, 404, 405 and 406, respectively, in the amino acid sequence of SEQ ID NO:14; i) amino acid residues 406, 411 and 412 (Epitope E) substituted at positions 415, 420 and 421, respectively, in the amino acid sequence of SEQ ID NO:14; j) amino acid residues 234, 310, 316, 483 and 492 (Epitope F) substituted at positions 234, 324, 330, 492 and 501, respectively, in the amino acid sequence of SEQ ID NO:14, and k) amino acid residues 327 and 403 (Epitope Fs) substituted at positions 341 and 412, respectively, in the amino acid sequence of SEQ ID NO:14, wherein amino acid residue numbering of (h)-(k) is based on the amino acid sequence of SEQ ID NOs:1-3.

Further provided herein is a norovirus P particle consisting of multiple copies of a norovirus P domain backbone from norovirus strain GII.3 (SEQ ID NO:14), in which one or more, in any combination, of the following sets of amino acid residues (a)-(k) are substituted into the norovirus P domain backbone from norovirus strain GII.3 to introduce one or more epitope in any combination, from one or more different norovirus strains having an amino acid sequence of SEQ ID Nos:1, 2, 3, 4, 5, 6, 7, 8, 9, 10, 11, 12, or 13, in any combination, as follows: a) amino acid residues 294, 296, 297, 298, 368 and 372 (Epitope A) substituted at positions 294, 310, 311, 312, 381 and 384, respectively, in the amino acid sequence of SEQ ID NO:14; b) amino acid residues 333 and 382 (Epitope B) substituted at positions 347 and 394, respectively, in the amino acid sequence of SEQ ID NO:14; c) amino acid residues 340 and 376 (Epitope C) substituted at positions 353 and 388, respectively, in the amino acid sequence of SEQ ID NO:14; d) amino acid residues 391, 393, 394, and 395 (Epitope D) substituted at positions 403, 404, 405 and 406, respectively, in the amino acid sequence of SEQ ID NO:14; e) amino acid residues 407, 412 and 413 (Epitope E) substituted at positions 415, 420 and 421, respectively, in the amino acid sequence of SEQ ID NO:14; f) amino acid residues 234, 310, 316, 484 and 493 (Epitope F) substituted at positions 234, 324, 330, 492 and 501, respectively, in the amino acid sequence of SEQ ID NO:14; and g) amino acid residues 327 and 404 (Epitope Fs) substituted at positions 341 and 412, respectively, in the amino acid sequence of SEQ ID NO:14, wherein amino acid residue numbering of (a)-(g) is based on the amino acid sequence of any of SEQ ID NOs:4-13; and h) amino acid residues 391, 393, 394 and 395 (Epitope D) substituted at positions 403, 404, 405 and 406, respectively, in the amino acid sequence of SEQ ID NO:14; i) amino acid residues 406, 411 and 412 (Epitope E) substituted at positions 415, 420 and 421, respectively, in the amino acid sequence of SEQ ID NO:14; j) amino acid residues 234, 310, 316, 483 and 492 (Epitope F) substituted at positions 234, 324, 330, 492 and 501, respectively, in the amino acid sequence of SEQ ID NO:14, and k) amino acid residues 327 and 403 (Epitope Fs) substituted at positions 341 and 412, respectively, in the amino acid sequence of SEQ ID NO:14, wherein amino acid residue numbering of (h)-(k) is based on the amino acid sequence of SEQ ID NOs:1-3, wherein the epitopes are presented on the P particle surface.

In addition, the present invention provides a mimitope comprising a norovirus epitope selected from the group consisting of: a) Epitope A; b) Epitope B; c) Epitope C; d) Epitope D; e) Epitope E; f) Epitope F; g) Epitope Fs; and h) any combination of (a) through (g) above.

It is understood that in any of the embodiments of this invention comprising the residues that make up Epitope A (294, 296, 297, 298, 368 and 372), amino acid 373 can be present in addition to the six listed residues, or absent. In embodiments of the invention comprising the amino acid sequence of SEQ ID NO:14, which is the GII.3 capsid protein sequence, the corresponding amino acid residue is 385. Thus, in embodiments in which residues are substituted to introduce Epitope A into the GII.3 backbone and amino acid 373 is included, the substitution is at the corresponding position 385.

In some embodiments, introduction of Epitope D can comprise substitutions at residues 391, 393, 394, 395 and 396, based on the amino acid sequence of SEQ ID Nos:4-13; however in embodiments in which substitutions are made to introduce Epitope D from a GII.4 norovirus strain into a GII.3 backbone, there is no corresponding position in the amino acid sequence of SEQ ID NO:14 for residue 396. There are corresponding positions 403, 404, 405, and 406 in the amino acid sequence of SEQ ID NO:14 for residues 391, 393, 394 and 395, respectively, in a GII.4 capsid protein sequence.

In an additional embodiment, the present invention provides a synthetic scaffold protein comprising amino acid residues from about 224 (e.g., from about 210, 211, 212, 213, 214, 215, 216, 217, 218, 219, 220, 221, 223, 224, 225, 226, 227, 228, 229, 230, 231, 232, 233, or 234 at the N terminus of the capsid protein segment) through about 516 (e.g., through about 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, etc. at the C terminus of the norovirus capsid protein segment) of a norovirus capsid protein, wherein amino acid residue numbering is based on the amino acid sequence of any of SEQ ID NOs:1-13 and wherein the norovirus capsid protein is a segment and not the full norovirus capsid protein.

The present invention further provides an isolated nucleic acid molecule encoding the chimeric norovirus capsid protein of this invention, a vector comprising the nucleic acid molecule of this invention and a cell comprising the capsid protein, nucleic acid molecule and/or vector of this invention.

In some embodiments, the present invention provides a Venezuelan Equine Encephalitis (VEE) replicon particle (VRP) comprising the nucleic acid molecule of this invention.

In some embodiments, the present invention provides a virus like particle (VLP) comprising the chimeric norovirus capsid protein of this invention.

The present invention also provides a composition comprising the chimeric norovirus capsid protein of this invention, the synthetic backbone molecule of this invention, the P particle of this invention, the mimitope of this invention, the nucleic acid molecule of this invention, the vector of this invention, the VRP of this invention and/or the VLP of this invention in a pharmaceutically acceptable carrier.

In some embodiments of the invention the individual and conformational epitopes of the norovirus capsid proteins can be presented on a synthetic backbone or support structure so that the epitopes within the synthetic backbone or support structure mimic the conformation and arrangement of the epitopes within the structure of the norovirus capsid protein, VLP or VRP.

In still further embodiments of the invention, the present invention provides peptide mimitopes (see, Meloen et al. (2000) *J. Mol. Recognit.* 13:352-359) that mimic the individual and conformational epitopes of the norovirus capsid proteins of the invention. Mimitopes may be identified using any technique known in the art, such as by surface stimulation, random peptide libraries or phage display libraries, using an antibody or antibodies to the individual and conformational epitopes of the chimeric norovirus capsid proteins of the invention.

In yet further embodiments of this invention a norovirus P particle (see, Tan et al. (2011) *J. Virol.* 85(2):753-764) is provided that presents the epitopes of the norovirus capsid proteins as described herein.

In an aspect of the chimeric VLP/VRP/virus vaccine approach of the invention, one or more of the identified potential neutralization epitopes from one or more donor strains is moved into any other GII.4 norovirus backbone strain to induce broad protection against multiple strains. In another aspect of the invention, moving epitope A from GII.4.1987 and epitope E from GII.4.2002 into the GII.4.2006 backbone induces a broadly blocking immune response in mice against GII.4 strains GII.4.1987, 2002, 2006, 2009, and 2012. Thus, by vaccine that incorporates epitope(s) from one or more circulating strains into the backbone of another strain can induce protection against multiple norovirus strains.

In a further aspect of the invention, in order to create a chimeric norovirus construct, the full-length ORF2 major capsid gene sequence from norovirus is either cloned from a patient sample or produced as a synthetic construct (e.g., from a commercial source). Natural or engineered endonuclease sites are used to insert sequence containing the desired epitope changes for one or more GII.4 strains. Alternatively, in yet another aspect of the invention, the full-length capsid may be synthesized (e.g., using a consensus sequence) with the desired sequence changes already present. After production of the desired full-length chimeric GII.4 norovirus capsid gene, this gene is then cloned into an expression vector. Upon expression, the VP1 major capsid protein self-assembles into VLPs, which can then be purified. Alternatively, VRPs expressing the major capsid protein can be produced and purified and subsequently used as a vaccine or used as a source of VLP production.

The term "chimeric norovirus capsid protein" and similar terms will be understood in the art to mean a norovirus capsid protein derived from a particular norovirus strain that contains single or multiple amino acid substitutions at various positions in which the amino acid substitution(s) is an amino acid(s) that is one from the corresponding position(s) of a norovirus capsid protein from a different norovirus strain. In representative embodiments, the amino acid substitution comprises a particular epitope from a norovirus strain different from that of the capsid protein in which the substitution is made. In further embodiments, the amino acid substitution(s) may be at amino acids 294, 296-298, 368 and 372 (with or without 373) (Epitope A) of the norovirus VP1 major capsid protein encoded by ORF2 of human norovirus (hNoV). In other embodiments, the substitution(s) may be at amino acids 333 and 382 (Epitope B) of the hNoV VP1 major capsid protein. In other embodiments, the substitution(s) may be at amino acids 340 and 376 (Epitope C) of the hNoV VP1 major capsid protein. In other embodiments, the substitution(s) may be at amino acids 391 and 393-395 or 391, 393-396 (Epitope D) of the hNoV VP1 major capsid protein. In other embodiments, the substitution(s) may be at amino acids 407, 412 and 413, or amino acids 406, 411 and 412, (Epitope E) of the hNoV VP1 major capsid protein. In still further embodiments, the amino acid substitution(s) may be at amino acid positions 234, 310, 316, 484 and 493 or 234, 310, 316, 483 and 492 (Epitope F) of the hNoV VP1 major capsid protein. In still further embodiments, the amino acid substitutions may comprise any two or more (e.g., 3, 4, 5, 6, 7, 8, 9, 10, etc.) of these epitopes, in any combination. In a particular embodiment, the combination of amino acid substitutions may be from Epitopes A and F.

The term "norovirus capsid protein backbone" and similar terms refer to the particular norovirus capsid protein from which a chimeric norovirus capsid protein is based. The norovirus capsid protein backbone may be from any genogroup, genotype and strain of hNoV. In an embodiment of the invention, the norovirus capsid protein backbone is from genogroup II and genotype 4 (GII.4) of hNoV. In an embodiment, the norovirus capsid protein backbone may be from GII.4-1974 (GenBank Access. No. ACT76139.1) (SEQ ID NO:1). In another embodiment, the norovirus capsid protein backbone may be from GII.4-1987 (GenBank Access. No. AAK50355.1) (SEQ ID NO:2). In another embodiment, the norovirus capsid protein backbone may be from GII.4-1997 (GenBank Access. No. AFJ04707.1) (SEQ ID NO:3). In another embodiment, the norovirus capsid protein backbone may be from GII.4-2002 (GenBank Access. No. AFJ04708.1) (SEQ ID NO:4). In another embodiment, the norovirus capsid protein backbone may be from GII.4-2004 (GenBank Access. No. AAZ31376.2) (SEQ ID NO:6). In another embodiment, the norovirus capsid protein backbone may be from GII.4-2005 (GenBank Access. No. BAE98194.1) (SEQ ID NO:7). In another embodiment, the norovirus capsid protein backbone may be from GII.4-2006 (GenBank Access. No. AFJ04709.1) (SEQ ID NO:8). In another embodiment, the norovirus capsid protein backbone may be from GII.4-2007 (GenBank Access. No. BAH56690.1) (SEQ ID NO:9). In another embodiment, the norovirus capsid protein backbone may be from GII.4-2008a (GenBank Access. No. ACX31885.1) (SEQ ID NO:10). In another embodiment, the norovirus capsid protein backbone may be from GII.4-2008s (GenBank Access. No. BAH30707.1) (SEQ ID NO:11). In another embodiment, the norovirus capsid protein backbone may be from GII.4-2009 (GenBank Access. No. ADD10375.1) (SEQ ID NO:12). In another embodiment, the norovirus capsid protein backbone may be from GII.4-2012 (GenBank Access. No. AFV08795.1) (SEQ ID NO:13).

In some embodiments, the norovirus capsid protein backbone can be from genogroup II and genotype 3 (GII.3) (GenBank Access. No. JQ743333), having the following amino acid sequence:

```
                                            (SEQ ID NO: 14)
MKMASNDAAPSNDGAAGLVPEINNEAMALDPVAGAAIAAPLTGQQNIID

PWIMNNFVQAPGGEFTVSPRNSPGEVLLNLELGPEINPYLAHLARMYNG

YAGGFEVQVVLAGNAFTAGKVIFAAIPPNFPIDNLSAAQITMCPHVIVD

VRQLEPINLPMPDVRNTFFHYNQDSDSRLRLIAMLYTPLRANNSGDDVF

TVSCRVLTRPSPDFSFNFLVPPTVESKTKLFTLPILTISEMSNSRFPVP

IDSLHTSPTENIVVQCQNGRVTLDGELMGTTQLLPSQICAFRGTLTRST

SRASDQADTPTPRLFNHRWHIQLDNLNGTPYDPAEDIPAPLGTPDFRGK

VFGVASQRNPDSTTRAHEAKVDTTSGRFTPKLGSLEITTESDDFDTNQS

TKFTPVGIGVDNEAEFQQWSLPNYSGQFTHNMNLAPAVAPNFPGEQLLF

FRSQLPSSGGWSNGVLDCLVPQEWVQHFYQESAPAQTQVALVRYVNPDT

GRVLFEAKLHKLGFMTIAKNGDSPITVPPNGYFRFESWVNPFYTLAPMG

TGNGRRRIQ.
```

The epitope of the chimeric norovirus capsid protein may be from any norovirus genogroup, genotype and strain, as long as it different from that of the norovirus capsid protein backbone. In a particular embodiment, wherein the norovirus capsid protein backbone is from GII.4-2006, the epitope is epitope A from GII.4-1987. In another particular embodiment, wherein the norovirus capsid protein backbone is from GII.4-2006, the epitopes can be a combination of Epitope A from GII.1987 and Epitope E from GII.4-2002.

The invention further provides a nucleic acid (e.g., isolated nucleic acid) encoding a chimeric norovirus capsid protein or a polypeptide of the invention.

The invention further provides a nucleic acid molecule (e.g., an isolated nucleic acid molecule) encoding a chimeric norovirus VLP, a chimeric norovirus VRP or a viral coat of a chimeric norovirus particle of the invention.

Also provided are vectors encoding the nucleic acid molecules of the invention.

Also provided are cells that comprise the vectors, nucleic acid molecules, norovirus epitopes, polypeptides, chimeric norovirus VLPs, chimeric norovirus VRPs or chimeric norovirus particles of the invention.

The invention also provides immunogenic compositions comprising the cells, vectors, nucleic acid molecules, noro-virus epitopes, chimeric norovirus capsid proteins, polypeptides, chimeric norovirus VLPs, chimeric norovirus VRPs, or chimeric norovirus particles of the invention in a pharmaceutically acceptable carrier. In embodiments, the immunogenic composition is monovalent. In embodiments, the immunogenic composition is multivalent for different norovirus serotypes.

The invention encompasses methods of vaccinating or immunizing a subject, e.g., to produce an immune response in the subject to norovirus, the method comprising administering to the subject an effective amount of a norovirus epitope, a chimeric norovirus capsid protein, a synthetic backbone molecule, a norovirus P particle, a mimitope, a chimeric norovirus VLP, a chimeric norovirus VRP or chimeric norovirus particle, nucleic acid molecule, vector, cell and/or composition of the invention.

The invention also encompasses methods of producing or eliciting an immune response to norovirus is a subject, the method comprising administering to the subject an effective amount of a norovirus epitope, a chimeric norovirus capsid protein, a synthetic backbone molecule, a norovirus P particle, a mimitope, a chimeric norovirus VLP, a chimeric norovirus VRP or chimeric norovirus particle, nucleic acid molecule, vector, cell and/or composition of the invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a fatty acid) and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, *In re Herz,* 537 F.2d 549, 551-52, 190 U.S.P.Q. 461, 463 (CCPA 1976) (emphasis in the original); see also MPEP § 2111.03. Thus, the term "consisting essentially of" when used in a claim of this invention is not intended to be interpreted to be equivalent to "comprising."

As used herein, the term "nucleic acid" encompasses both RNA and DNA, including cDNA, genomic DNA, synthetic (e.g., chemically synthesized) DNA and chimeras of RNA and DNA. The nucleic acid may be double-stranded or single-stranded. The nucleic acid may be synthesized using nucleotide analogs or derivatives (e.g., inosine or phosphorothioate nucleotides). Such nucleotides can be used, for example, to prepare nucleic acids that have altered base-pairing abilities or increased resistance to nucleases.

As used herein, the term "polypeptide" encompasses both peptides and proteins (including fusion proteins), unless indicated otherwise.

A "fusion protein" is a polypeptide produced when two heterologous nucleotide sequences or fragments thereof coding for two (or more) different polypeptides not found fused together in nature are fused together in the correct translational reading frame.

A "recombinant" nucleic acid, polynucleotide or nucleotide sequence is one produced by genetic engineering techniques.

A "recombinant" polypeptide is produced from a recombinant nucleic acid, polypeptide or nucleotide sequence.

As used herein, an "isolated" polynucleotide (e.g., an "isolated nucleic acid" or an "isolated nucleotide sequence") means a polynucleotide at least partially separated from at least some of the other components of the naturally occurring organism or virus, for example, the cell or viral structural components or other polypeptides or nucleic acids commonly found associated with the polynucleotide. Optionally, but not necessarily, the "isolated" polynucleotide is present at a greater concentration (i.e., is enriched) as compared with the starting material (e.g., at least about a two-fold, three-fold, four-fold, ten-fold, twenty-fold, fifty-fold, one-hundred-fold, five-hundred-fold, one thousand-fold, ten thousand-fold or greater concentration). In representative embodiments, the isolated polynucleotide is at least about 1%, 5%, 10%, 20%, 30%, 40%, 50%, 60%, 70%, 80%, 90%, 95% or more pure.

An "isolated" polypeptide means a polypeptide that is at least partially separated from at least some of the other components of the naturally occurring organism or virus, for example, the cell or viral structural components or other polypeptides or nucleic acids commonly found associated with the polypeptide. Optionally, but not necessarily, the "isolated" polypeptide is present at a greater concentration (i.e., is enriched) as compared with the starting material (e.g., at least about a two-fold, three-fold, four-fold, ten-fold, twenty-fold, fifty-fold, one-hundred-fold, five-hundred-fold, one thousand-fold, ten thousand-fold or greater concentration). In representative embodiments, the isolated polypeptide is at least about 1%, 5%, 10%, 20%, 30%, 40%, 50%, 60%, 70%, 80%, 90%, 95% or more pure.

Furthermore, an "isolated" cell is a cell that has been partially or completely separated from other components with which it is normally associated in nature. For example, an isolated cell can be a cell in culture medium and/or a cell in a pharmaceutically acceptable carrier.

The terms "immunogen" and "antigen" are used interchangeably herein and mean any compound (including polypeptides) to which a cellular and/or humoral immune response can be directed. In particular embodiments, an immunogen or antigen can induce a protective immune response against the effects of norovirus infection.

"Effective amount" as used herein refers to an amount of a vector, nucleic acid molecule, epitope, polypeptide, cell, composition or formulation of the invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation.

The term "immunogenic amount" or "effective immunizing dose," as used herein, unless otherwise indicated, means an amount or dose sufficient to induce an immune response (which can optionally be a protective response) in the treated subject that is greater than the inherent immunity of non-immunized subjects. An immunogenic amount or effective immunizing dose in any particular context can be routinely determined using methods known in the art.

The terms "vaccine," "vaccination," "vaccinating," immunizing" and "immunization" are well-understood in the art, and are used interchangeably herein. For example, the terms vaccine, vaccination or immunization can be understood to be a process or composition that produces an immune response to an antigen introduced into the subject via vaccination or immunization of the subject and/or increases a subject's immune reaction or response to an immunogen (e.g., by providing an active immune response), and therefore its ability to resist, overcome and/or recover from infection (i.e., a protective immune response).

By the terms "treat," "treating" or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay in the progression of the disease or disorder. In representative embodiments, the terms "treat," "treating" or "treatment of" (and grammatical variations thereof) refer to a reduction in the severity of viremia and/or a delay in the progression of viremia, with or without other signs of clinical disease.

A "treatment effective" amount as used herein is an amount that is sufficient to treat (as defined herein) the subject. Those skilled in the art will appreciate that the therapeutic effects need not be complete or curative, as long as some benefit is provided to the subject.

The terms "prevent," "preventing" or "prevention of" (and grammatical variations thereof) refer to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. In representative embodiments, the terms "prevent," "preventing" or "prevention of" (and grammatical variations thereof) refer to prevention and/or delay of the onset and/or progression of viremia in the subject, with or without other signs of clinical disease. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention.

A "prevention effective" amount as used herein is an amount that is sufficient to prevent (as defined herein) the disease, disorder and/or clinical symptom in the subject. Those skilled in the art will appreciate that the level of prevention need not be complete, as long as some benefit is provided to the subject.

The efficacy of treating and/or preventing norovirus infection by the methods of the present invention can be determined by detecting a clinical improvement as indicated by a change in the subject's symptoms and/or clinical parameters (e.g., viremia), as would be well known to one of skill in the art.

Unless indicated otherwise, the terms "protect," "protecting," "protection" and "protective" (and grammatical variations thereof) encompass both methods of preventing and treating norovirus infection in a subject, whether against one or multiple strains, genotypes or genogroups of norovirus.

The terms "protective" immune response or "protective" immunity as used herein indicates that the immune response confers some benefit to the subject in that it prevents or reduces the incidence and/or severity and/or duration of disease or any other manifestation of infection. For example, in representative embodiments, a protective immune response or protective immunity results in reduced viremia, whether or not accompanied by clinical disease. Alternatively, a protective immune response or protective immunity may be useful in the therapeutic treatment of existing disease.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "subject" of the invention includes any animal susceptible to norovirus infection. Such a subject is generally a mammalian subject (e.g., a laboratory animal such as a rat, mouse, guinea pig, rabbit, primates, etc.), a farm or commercial animal (e.g., a cow, horse, goat, donkey, sheep, etc.), or a domestic animal (e.g., cat, dog, ferret, etc.). In particular embodiments, the subject is a primate subject, a non-human primate subject (e.g., a chimpanzee, baboon, monkey, gorilla, etc.) or a human. Subjects of the invention can be a subject known or believed to be at risk of infection by norovirus. Alternatively, a subject according to the invention can also include a subject not previously known or suspected to be infected by norovirus or in need of treatment for norovirus infection.

Subjects may be treated for any purpose, such as for eliciting a protective immune response or for eliciting the production of antibodies in that subject, which antibodies can be collected and used for other purposes such as research or diagnostic purposes or for administering to other subjects to produce passive immunity therein, etc.

Subjects include males and/or females of any age, including neonates, juvenile, mature and geriatric subjects. With respect to human subjects, in representative embodiments, the subject can be an infant (e.g., less than about 12 months, 10 months, 9 months, 8 months, 7 months, 6 months, or younger), a toddler (e.g., at least about 12, 18 or 24 months and/or less than about 36, 30 or 24 months), or a child (e.g., at least about 1, 2, 3, 4 or 5 years of age and/or less than about 14, 12, 10, 8, 7, 6, 5, or 4 years of age). In embodiments of the invention, the subject is a human subject that is from about 0 to 3, 4, 5, 6, 9, 12, 15, 18, 24, 30, 36, 48 or 60 months of age, from about 3 to 6, 9, 12, 15, 18, 24, 30, 36, 48 or 60 months of age, from about 6 to 9, 12, 15, 18, 24, 30, 36, 48 or 60 months of age, from about 9 to 12, 15, 18, 24, 30, 36, 48 or 60 months of age, from about 12 to 18, 24, 36, 48 or 60 months of age, from about 18 to 24, 30, 36, 48 or 60 months of age, or from about 24 to 30, 36, 48 or 60 months of age.

A "subject in need" of the methods of the invention can be a subject known to be, or suspected of being, infected with, or at risk of being infected with, norovirus.

Pharmaceutical formulations (e.g., immunogenic formulation) comprising the norovirus epitopes, chimeric norovirus capsid proteins, polypeptides, chimeric norovirus VLPs, chimeric norovirus VRPs or chimeric norovirus particles, nucleic acids, vectors, cells or compositions of the invention and a pharmaceutically acceptable carrier are also provided, and can be formulated for administration in a pharmaceutical carrier in accordance with known techniques. See, e.g., Remington, *The Science and Practice of Pharmacy* (latest edition). In the manufacture of a pharmaceutical composition according to embodiments of the present invention, the composition of the invention is typically admixed with, inter alia, a pharmaceutically acceptable carrier. By "pharmaceutically acceptable carrier" is meant a carrier that is compatible with other ingredients in the pharmaceutical composition and that is not harmful or deleterious to the subject. The carrier may be a solid or a liquid, or both, and is preferably formulated with the composition of the invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients. In certain embodiments, the pharmaceutically acceptable carrier is sterile and would be deemed suitable for administration into human subjects according to regulatory guidelines for pharmaceutical compositions comprising the carrier.

Furthermore, a "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include any of the standard pharmaceutical carriers such as phosphate buffered saline solutions, water, emulsions such as oil/water emulsion, microemulsions and various types of wetting agents.

In some embodiments, the compositions of the invention can further comprise one or more than one adjuvant. The adjuvants of the present invention can be in the form of an amino acid sequence, and/or in the form or a nucleic acid encoding an adjuvant. When in the form of a nucleic acid, the adjuvant can be a component of a nucleic acid encoding the polypeptide(s) or fragment(s) or epitope(s) and/or a separate component of the composition comprising the nucleic acid encoding the polypeptide(s) or fragment(s) or epitope(s) of the invention. According to the present invention, the adjuvant can also be an amino acid sequence that is a peptide, a protein fragment or a whole protein that functions as an adjuvant, and/or the adjuvant can be a nucleic acid encoding a peptide, protein fragment or whole protein that functions as an adjuvant. As used herein, "adjuvant" describes a substance, which can be any immunomodulating substance capable of being combined with a composition of the invention to enhance, improve or otherwise modulate an immune response in a subject.

In further embodiments, the adjuvant can be, but is not limited to, an immunostimulatory cytokine (including, but not limited to, GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules), SYNTEX adjuvant formulation 1 (SAF-1) composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Suitable adjuvants also include an aluminum salt such as aluminum hydroxide gel (alum), aluminum phosphate, or algannmulin, but may also be a salt of calcium, iron or zinc, or may be an insoluble suspension of acylated tyrosine, or acylated sugars, cationically or anionically derivatized polysaccharides, or polyphosphazenes.

Other adjuvants are well known in the art and include without limitation MF 59, LT-K63, LT-R72 (Pal et al., Vaccine 24(6):766-75 (2005)), QS-21, Freund's adjuvant (complete and incomplete), aluminum hydroxide, N-acetyl-muramyl-L-threonyl-D-isoglutamine (thr-MDP), N-acetyl-normuramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion.

Additional adjuvants can include, for example, a combination of monophosphoryl lipid A, preferably 3-de-O-acylated monophosphoryl. lipid A (3D-MPL) together with an aluminum salt. An enhanced adjuvant system involves the combination of a monophosphoryl lipid A and a saponin derivative, particularly the combination of QS21 and 3D-MPL as disclosed in PCT publication number WO 94/00153, or a less reactogenic composition where the QS21 is quenched with cholesterol as disclosed in PCT publication number WO 96/33739. A particularly potent adjuvant formulation involving QS21 3D-MPL & tocopherol in an oil in water emulsion is described in PCT publication number WO 95/17210. In addition, the nucleic acid compositions of the invention can include an adjuvant by comprising a nucleotide sequence encoding the antigen and a nucleotide sequence that provides an adjuvant function, such as CpG sequences. Such CpG sequences, or motifs, are well known in the art.

An adjuvant for use with the present invention, such as, for example, an immunostimulatory cytokine, can be administered before, concurrent with, and/or within a few hours, several hours, and/or 1, 2, 3, 4, 5, 6, 7, 8, 9, and/or 10 days before and/or after the administration of a composition of the invention to a subject.

Furthermore, any combination of adjuvants, such as immunostimulatory cytokines, can be co-administered to the subject before, after and/or concurrent with the administration of an immunogenic composition of the invention. For example, combinations of immunostimulatory cytokines, can consist of two or more immunostimulatory cytokines, such as GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules. The effectiveness of an adjuvant or combination of adjuvants can be determined by measuring the immune response produced in response to administration of a composition of this invention to a subject with and without the adjuvant or combination of adjuvants, using standard procedures, as described herein and as known in the art.

In embodiments of the invention, the adjuvant comprises an alphavirus adjuvant as described, for example in U.S. Pat. No. 7,862,829.

Boosting dosages can further be administered over a time course of days, weeks, months or years. In chronic infection, initial high doses followed by boosting doses may be advantageous.

The pharmaceutical formulations of the invention can optionally comprise other medicinal agents, pharmaceutical agents, stabilizing agents, buffers, carriers, diluents, salts, tonicity adjusting agents, wetting agents, and the like, for example, sodium acetate, sodium lactate, sodium chloride, potassium chloride, calcium chloride, sorbitan monolaurate, triethanolamine oleate, etc.

For injection, the carrier will typically be a liquid. For other methods of administration, the carrier may be either solid or liquid. For inhalation administration, the carrier will be respirable, and is typically in a solid or liquid particulate form.

The compositions of the invention can be formulated for administration in a pharmaceutical carrier in accordance with known techniques. See, e.g., Remington, The Science and Practice of Pharmacy ($9^{th}$ Ed. 1995). In the manufacture of a pharmaceutical composition according to the invention, the VLPs are typically admixed with, inter alia, an acceptable carrier. The carrier can be a solid or a liquid, or both, and is optionally formulated with the compound as a unit-dose formulation, for example, a tablet. A variety of pharmaceutically acceptable aqueous carriers can be used, e.g., water, buffered water, 0.9% saline, 0.3% glycine, hyaluronic acid, pyrogen-free water, pyrogen-free phosphate-buffered saline solution, bacteriostatic water, or Cremophor EL[R] (BASF, Parsippany, N.J.), and the like. These compositions can be sterilized by conventional techniques. The formulations of the invention can be prepared by any of the well-known techniques of pharmacy.

The pharmaceutical formulations can be packaged for use as is, or lyophilized, the lyophilized preparation generally being combined with a sterile aqueous solution prior to administration. The compositions can further be packaged in unit/dose or multi-dose containers, for example, in sealed ampoules and vials.

The pharmaceutical formulations can be formulated for administration by any method known in the art according to conventional techniques of pharmacy. For example, the compositions can be formulated to be administered intranasally, by inhalation (e.g., oral inhalation), orally, buccally (e.g., sublingually), rectally, vaginally, topically, intrathecally, intraocularly, transdermally, by parenteral administration (e.g., intramuscular [e.g., skeletal muscle], intravenous, subcutaneous, intradermal, intrapleural, intracerebral and intra-arterial, intrathecal), or topically (e.g., to both skin and mucosal surfaces, including airway surfaces).

For intranasal or inhalation administration, the pharmaceutical formulation can be formulated as an aerosol (this term including both liquid and dry powder aerosols). For example, the pharmaceutical formulation can be provided in a finely divided form along with a surfactant and propellant. Typical percentages of the composition are 0.01-20% by weight, preferably 1-10%. The surfactant is generally non-toxic and soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1-20% by weight of the composition, preferably 0.25-5%. The balance of the composition is ordinarily propellant. A carrier can also be included, if desired, as with lecithin for intranasal delivery. Aerosols of liquid particles can be produced by any suitable means, such as with a pressure-driven aerosol nebulizer or an ultrasonic nebulizer, as is known to those of skill in the art. See, e.g., U.S. Pat. No. 4,501,729. Aerosols of solid particles can likewise be produced with any solid particulate medicament aerosol generator, by techniques known in the pharmaceutical art. Intranasal administration can also be by droplet administration to a nasal surface.

Injectable formulations can be prepared in conventional forms, either as liquid solutions or suspensions, solid forms suitable for solution or suspension in liquid prior to injection, or as emulsions. Alternatively, one can administer the pharmaceutical formulations in a local rather than systemic manner, for example, in a depot or sustained-release formulation.

Extemporaneous injection solutions and suspensions can be prepared from sterile powders, granules and tablets of the kind previously described. For example, an injectable, stable, sterile formulation of the invention in a unit dosage form in a sealed container can be provided. The formulation can be provided in the form of a lyophilizate, which can be reconstituted with a suitable pharmaceutically acceptable carrier to form a liquid composition suitable for injection into a subject. The unit dosage form can be from about 1 μg to about 10 grams of the formulation. When the formulation is substantially water-insoluble, a sufficient amount of emulsifying agent, which is pharmaceutically acceptable, can be included in sufficient quantity to emulsify the formulation in an aqueous carrier. One such useful emulsifying agent is phosphatidyl choline.

Pharmaceutical formulations suitable for oral administration can be presented in discrete units, such as capsules, cachets, lozenges, or tables, as a powder or granules; as a solution or a suspension in an aqueous or non-aqueous liquid; or as an oil-in-water or water-in-oil emulsion. Oral delivery can be performed by complexing a compound(s) of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the protein(s) and a suitable carrier (which may contain one or more accessory ingredients as noted above). In general, the pharmaceutical formulations are prepared by uniformly and intimately admixing the compound(s) with a liquid or finely divided solid carrier, or both, and then, if necessary, shaping the resulting mixture. For example, a tablet can be prepared by compressing or molding a powder or granules, optionally with one or more accessory ingredients. Compressed tablets are prepared by compressing, in a suitable machine, the formulation in a free-flowing form, such as a powder or granules optionally mixed with a binder, lubricant, inert diluent, and/or surface active/dispersing agent(s). Molded tablets are made by molding, in a suitable machine, the powdered protein moistened with an inert liquid binder.

Pharmaceutical formulations suitable for buccal (sublingual) administration include lozenges comprising the compound(s) in a flavored base, usually sucrose and acacia or tragacanth; and pastilles in an inert base such as gelatin and glycerin or sucrose and acacia.

Pharmaceutical formulations suitable for parenteral administration can comprise sterile aqueous and non-aqueous injection solutions, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical formulations suitable for rectal administration are optionally presented as unit dose suppositories. These can be prepared by admixing the active agent with one or more conventional solid carriers, such as for example, cocoa butter and then shaping the resulting mixture.

Pharmaceutical formulations suitable for topical application to the skin preferably take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical formulation of the present invention with a lipophilic reagent (e.g., DMSO) that is capable of passing into the skin.

Pharmaceutical formulations suitable for transdermal administration can be in the form of discrete patches adapted to remain in intimate contact with the epidermis of the subject for a prolonged period of time. Formulations suitable for transdermal administration can also be delivered by iontophoresis (see, for example, *Pharmaceutical Research* 3:318 (1986)) and typically take the form of a buffered aqueous solution of the compound(s). Suitable formulations can comprise citrate or bis\tris buffer (pH 6) or ethanol/water and can contain from 0.1 to 0.2M active ingredient.

Further, the composition can be formulated as a liposomal formulation. The lipid layer employed can be of any conventional composition and can either contain cholesterol or can be cholesterol-free. The liposomes that are produced can be reduced in size, for example, through the use of standard sonication and homogenization techniques.

The liposomal formulations can be lyophilized to produce a lyophilizate which can be reconstituted with a pharmaceutically acceptable carrier, such as water, to regenerate a liposomal suspension.

The immunogenic formulations of the invention can optionally be sterile, and can further be provided in a closed pathogen-impermeable container.

In embodiments of the invention, the dosage of a virus particle of this invention can be in a range of about $10^3$ to about $10^8$ plaque forming units (PFUs). In embodiments of this invention, the dosage of a VLP of this invention can be in a range of about 5 micrograms to 5 milligrams. In embodiments of this invention, the dosage of a protein of this invention can be in a range of about 10 to about $10^5$ micrograms+/− adjuvant.

The present subject matter will be now be described more fully hereinafter with reference to the accompanying EXAMPLES, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

EXAMPLES

The following examples provide illustrative embodiments. Certain aspects of the following examples are disclosed in terms of techniques and procedures found or contemplated by the present inventors to work well in the practice of the embodiments. In light of the present disclosure and the general level of skill in the art, those of skill will appreciate that the following examples are intended to be exemplary only and that numerous changes, modifications, and alterations can be employed without departing from the scope of the presently claimed subject matter.

Example 1

Using an in vitro surrogate neutralization assay to measure antibody blockade of NoV virus-like particle (VLP) binding to carbohydrate ligand, shown to correlate with protection from infection, four evolving "blockade" antibody epitopes have been characterized. Epitope A is immunodominant (~40% of the serum blockade antibody response) and changes with each epidemiologically significant strain. Epitope D lies along the ridge of the carbohydrate-binding domain and is both a blockade antibody epitope and a mediator of carbohydrate binding affinities. Epitopes A and D face the most exterior part of the viral particle (the P2 subdomain) and are easily accessible to potent blockade antibodies. Epitope E is lateral to D and is less exposed to the surface. Finally, Epitope F is highly conserved across GII.4 strains and its structural location is unknown. NoV infection and vaccination elicits antibodies to subdominant Epitope F. Residues outside the antibody-binding site (NERK motif) are highly conserved and regulate access to F by allosteric effects on particle conformation with an unclear mechanism. The high degree of conservation of Epitope F has limited the effectiveness of bioinformatics approaches to identifying Epitope F and additional NERK motif residues, although this approach was instrumental to predict evolving blockade antibody epitopes that were further verified by testing chimeric VLPs and monoclonal antibodies (mAbs).

In this study, we use norovirus virus-like particles to identify key residues of a conserved GII.4 blockade antibody epitope. Further, we identify an additional GII.4 blockade antibody epitope to be occluded, with antibody access governed by temperature and particle dynamics. These findings provide additional support for particle-conformation based presentation of binding residues mediated by a particle "breathing core". Together, these data suggest that limiting antibody access to blockade antibody epitopes may be a frequent mechanism of immune evasion for GII.4 human NoVs. Mapping of blockade antibody epitopes, the interaction between adjacent epitopes on the particle and the breathing core that mediates antibody access to epitopes, provides greater mechanistic understanding of epitope camouflage strategies utilized by human viral pathogens to evade immunity.

Figure 8:
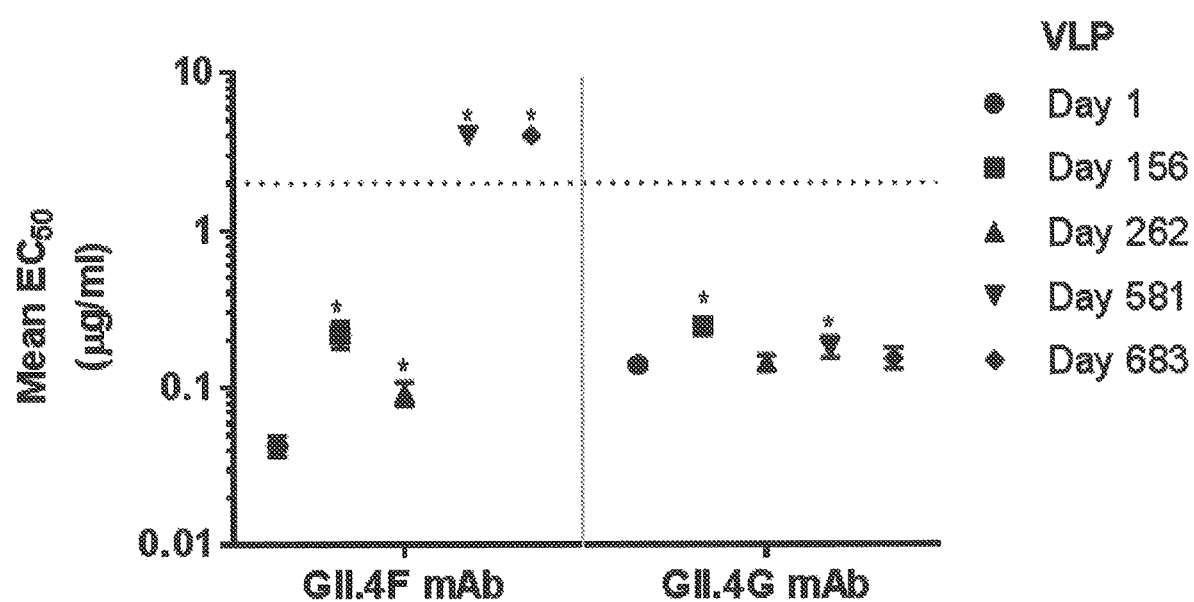
FIG. 8: The conserved GII.4 blockade epitope for human monoclonal antibody GII.4F was lost only after long-term in vivo evolution of a GII.4.2006a human norovirus strain within an immunocompromised host. Virus-like particles representing norovirus sequences isolated from a transplant patient over a 683-day period were evaluated for binding to human mAb GII.4F and mouse mAb GII.4G by EIA. After at least 581 days of in vivo evolution, capsid sequence changes resulted in loss of binding of GII.4F but not GII.4G. Error bars represent 95% confidence intervals. *Significantly different from Day 1.
Figure 9A:
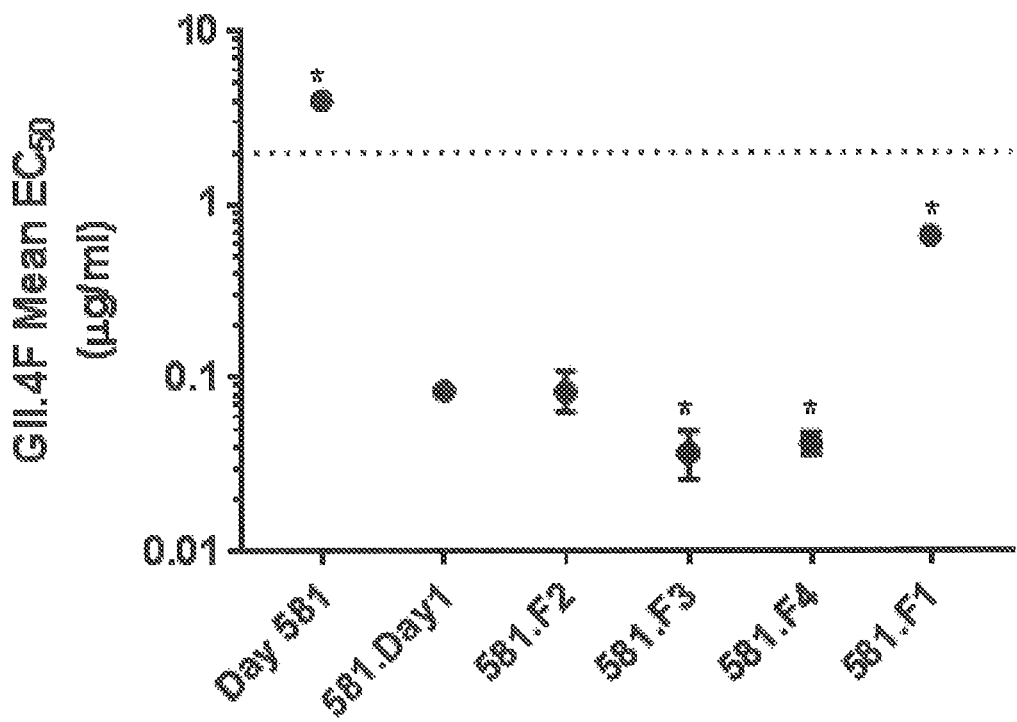
FIGS. 9A-9B: Valine at residues 327 and 404 is key to GII4.F binding. To map the epitope for GII.4F, amino acid changes in the capsid protein between Day 1 and Day 581 strains were compared and sets of changes introduced into the 581 backbone sequence. Chimeric VLPs were evaluated for GII.4F binding by EIA and $EC_{50}$ titers determined. VLPs with binding below the limit of detection are assigned an $EC_{50}$ of 4.
Figure 9B:
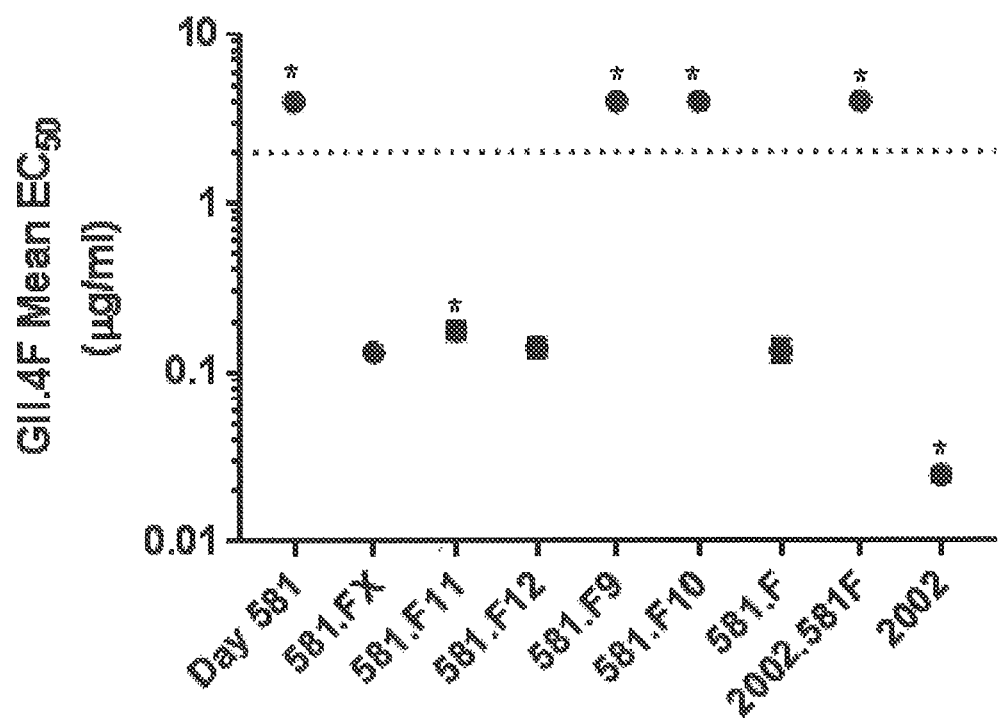

Residues 327 and 404 are key binding sites of the GII.4 conserved blockade antibody epitope. GII.4F or GII.4G mAbs recognize two spatially close conserved blockade epitopes with restricted access based on particle conformation. The spatial location of targeted residues (Table 1) remains unknown, although NERK motif modifications in part regulate access to these epitopes. To map GII.4F or GII.4G residues, VLPs representing time-ordered GII.4.2006a norovirus strains that evolved in stool samples from an immunocompromised transplant patient over 683 days were synthesized, expressed and characterized for binding of GII.4F or GII.4G mAbs by EIA (FIG. 1). GII.4G mAb appears to bind to a unique conserved epitope, designated G, that may overlap Epitope F and was preserved during the period of monitoring, as assessed by both binding and blockade assays. In contrast, by day 581 evolution in Epitope F resulted in loss of binding of mAb GII.4F (FIG. 8). Day 581 VLP is the first identified GII.4 VLP not to react with mAb GII.4F. Amino acid substitutions associated with in vivo evolution occurred at twenty-two residues within the major capsid protein between day 1 and 581 of monitoring. Fifteen of the changed residues were in the P2 domain, potentially influencing blockade antibody epitopes. To map the epitope for mAb GII.4F, amino acid changes in the capsid protein were compared and sets of changes introduced into the day 581 backbone sequence (FIG. 2). Restoring the fourteen residues in 581.F2 gained binding of NVB 71 similarly to restoring all twenty-two residues that differed between day 1 and day 581 (581.Day1) (FIG. 9A). 581.F3 and F4, but not 581.F1, improved GII.4F binding in EIA. A five-residue exchange of F2 residues (234, 327, 340, 391 and 404) into the Day 581 backbone (581.FX) gained GII.4F binding and was further analyzed (FIG. 2 and FIG. 9B). Only VLPs with valines at positions 327 and 404 were sufficient to restore GII.4F binding (581.F). Conversely, when substituting V327 to K and V404 to E in GII.4.2002 (2002.581F), GII.4F binding was lost, confirming V327 and V404 are critical key residues of the conserved GII.4 blockade Ab Epitope F. Homology modeling of residues 327 and 404 shows that they form a conformational epitope proximal to evolving blockade antibody Epitope E. In the model, K327 directly interacts with E404 via electrostatic interaction, which likely rearranges the local structural neighborhood of Epitope F. In addition, modeling of the hydrogen bond networks between residues V327, Q401 and V404 suggests that three hydrogen bonds are formed in the Day 262 isolate (FIG. 3, dashed), while two additional hydrogen bonds (dashed lines) are formed in the Day 581 model among 327K, 401Q, and 404E. These additional bonds likely contribute to the loss of GII.4F binding to Day 581 VLPs.

Residue 234 influences GII.4F mAb access to the conserved blockade antibody epitope. As previously described, GII.4F mAb blockade potency is mediated by both the number of accessible binding sites as well as by the affinity of the antibody for the target epitope. To understand the contributions to binding of the five residues included in 581.FX, chimeric VLPs containing admixtures of residues 234, 327, 340, 391 and 404 (581.F9-F12) were tested for GII.4F mAb binding by EIA. VLPs are composed of 90 copies of a dimer of the capsid protein, accounting for a total of 180 copies of non-quaternary epitopes. Changes in $B_{max}$ (maximum number of binding sites) reflect access to binding of antibody to the these epitopes. $K_D$ (affinity) is dependent on the strength of molecular interaction between the epitope and the antibody. Changes in residues 340 and 391 did not affect GII.4F mAb affinity or access (FIG. 4). The $K_D$ was consistent between the VLPs with valines at positions 327 and 404 (1.1 nM), indicating that these residues define part of GII.4 Epitope F. V234 did not associate with changes in $K_D$. The V234 VLPs (581.FX and 581.F12) (FIG. 4) had higher $B_{max}$ than 581.F (K327V, E404V), indicating that 234 may be influencing GII.4F mAb binding via long-range allosteric effects, as described for the NERK motif. The NERK motif and residue 234 (the "breathing core") are distal to the epitope and near the dimer interface (FIG. 5).

Antibody access to evolving blockade antibody Epitope E depends on global particle and local conformation. Epitope E, like Epitope F, is lateral to Epitopes A and D, which line the outer most surface of the viral particle. Epitope E and F residues are 7-23 angstroms of each other. To determine if particle conformation also regulates antibody access to Epitope E, GII.4.2002 blockade by mAb GII.4E (Table 1) was tested at room temperature and 37° C., as previously described. Increased temperature of incubation resulted in a 2.7-fold decrease in $EC_{50}$ titer and a 3.2-fold increase in blockade curve slope for GII.4E blockade of GII.4.2002 (FIG. 6A), indicating GII.4E access to evolving blockade Epitope E improves at higher temperature. These results are similar to those reported for Epitopes F and G blockade and suggest particle dynamics also regulate antibody access to Epitope E.

Figure 6B:
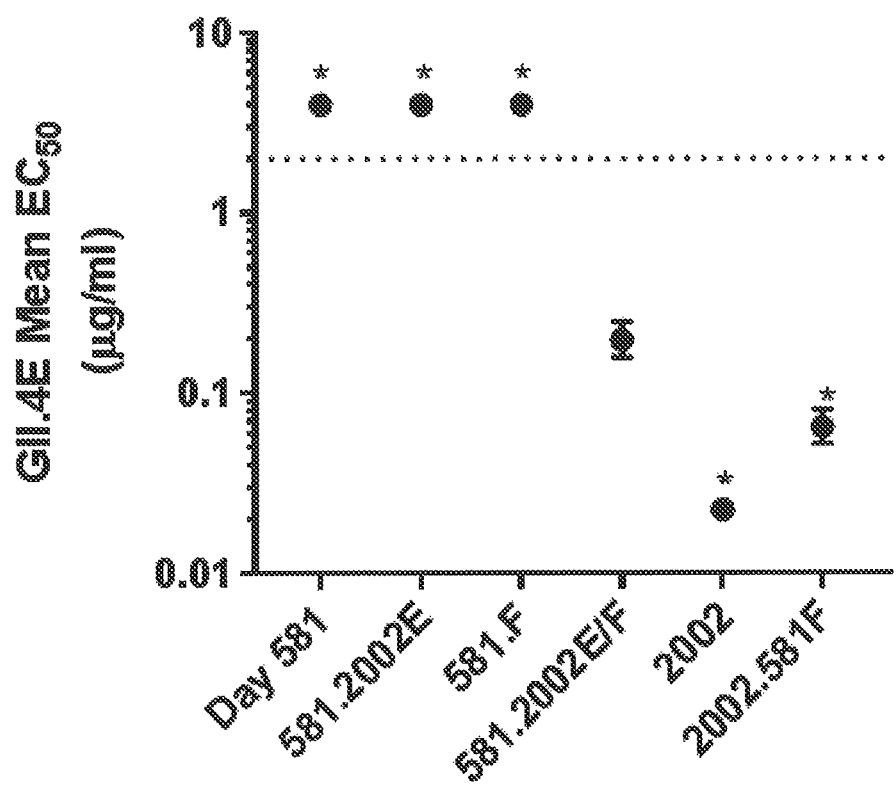

To explore any direct or indirect interaction between Epitopes E and F, a series of VLPs with exchanged Epitopes E, F, or both were tested for EIA binding with mAb GII.4E (FIG. 6B). Exchange of either Epitope E (581.2002E) or F (581F) residues from GII.4.2002 into the 581 backbone did not confer GII.4E binding. However, exchange of both Epitope E and F (581.2002E/F) resulted in gain of GII.4E binding. Conversely, exchange of Epitope F residues from 581 into the 2002 (2002.581F) backbone increased 2.9-fold the $EC_{50}$ titer of GII.4E for GII.4.2002. These data indicate that Epitope F residues effect the binding of Epitope E antibodies. To distinguish the effects of Epitope E and F residues on GII.4E binding, chimeric VLPs were tested for GII.4E binding by EIA and $B_{max}$ and $K_D$ values were calculated (FIG. 6C). Exchange of Day 581 Epitope F residues into the 2002 backbone (2002.581F) did not change the $K_D$ (0.33 nM) for GII.4E but did decrease the $B_{max}$. Therefore, Epitope F residues are not part of Epitope E but instead regulate GII.4E epitope access. These data indicate that local particle conformation also regulates antibody access to blockade epitopes.

Blockade antibody responses are proposed correlates of human norovirus protective immunity. Elucidation of the specific epitopes correlated with protection could facilitate vaccine design strategies. NoV infection elicits a skewed blockade antibody response to the hypervariable Epitope A of the infecting strain. Similarly, in human trials NoV multivalent VLP vaccination recalls a memory response to previous strain Epitope A. The ability to harness preferential antigen presentation on VLP vaccines could selectively drive vaccine immune responses away from the hypervariable epitopes and toward cross-protective conserved epitopes. This report is the first to map key amino acids comprising part of a conserved GII.4 NoV blockade antibody epitope (F) recognized by a human monoclonal antibody, identify two additional conformation-dependent epitopes (E and G) and then to expand the set of residues that influence particle dynamics and antibody access to occluded blockade antibody epitopes. These are important steps in designing an engineered cross-protective norovirus VLP vaccine candidate.

The implication of NoV infection in immunocompromised individuals is an expanding area of study. Virus sequencing from serial stool samples indicates that even under the atypical (reduced) immune pressure exerted in an immunocompromised patient, NoV continues to evolve via antigenic drift at blockade antibody epitopes (FIG. 1). This process mimics viral evolution within the general population that leads to new virus emergence. An extended period of in vivo evolution allowed the first identified change in Epitope F. Valine at positions 327 and 404 are parts of Epitope F and are conserved across GII.4 NoV strains circulating from 1974 until 2015. Occluded epitopes of other human RNA viruses are essential for receptor binding, viral fusion, capsid assembly/disassembly; functions essential for infection/replication. It is unknown if particle conformation plays similar roles in the norovirus life cycle or whether antibody binding to Epitope F affects particle dynamics necessary for ligand binding or sterically blocks ligand interaction. The primary limitation to this study is the lack of a reverse genetics system to test these possibilities. The newly developed NoV replication system may someday be amenable to a reverse genetics approach to studying viral mutants and elucidate the role of Epitope F residues. It is possible that V327 and V404 are not part of Epitope F, but instead, mutations at these residues such as those observed in this study could prevent conformational transitions necessary for antibody binding. However, this explanation is unlikely, as antibody access to the overlapping Epitope G and the neighboring Epitope E remains temperature sensitive, indicating particle plasticity is maintained in the 581 VLP (327K.404E).

Unlike 327 and 404, residue 234 is buried near the dimer interface and does not participate in GII.4F binding. Instead, 234 regulates antibody access to occluded epitopes by mediating particle conformation, similarly to what has been described for residues 310, 316, 484 and 494 (NERK motif). These data indicate that 234, the NERK motif, and possibly other unidentified amino acids form a "breathing core" that works in concert to regulate global particle structure driving antigenicity and ligand binding (FIG. 5). Mutations in the breathing core could modulate epitope presentation, altering the effectiveness of antibody responses in protection from infection and influencing the repertoire of antibodies made following vaccination and infection. The NERK motif is highly conserved in GII.4 strains from 1974-2006. Contemporary strains GII.4.2009 and 2012 both introduced mutation at residue 310, which resulted in altered antibody access to Epitope F. Although speculative, changes at 310 may have been driven by pressure to alter protection of Epitope F. Further, controlling particle dynamics may have practical implications for VLP immunogens where viral entry is not maintained. An engineered VLP designed to have decreased fluctuation by temperature could improve thermostability and shelf life of VLP-based vaccines, as well as enhance antigen presentation stability.

Based on our existing panels of antibodies, presentation of Epitopes A and D is not particle conformation dependent and changes in the NERK motif do not effect blockade potency of antibodies to these epitopes. The findings presented here indicate that the delineating factor between occluded and non-occluded epitopes is likely location on the viral particle. Evolving blockade Epitope E lies near the transition from the most-surface exposed P2 subdomain of the capsid protein and the less-surface exposed P1 subdomain. Epitope E is variable between pandemic strains and antibody access is occluded. Although a virion has the same number of Epitopes A, E, F and G, antibodies to Epitope E, F and G are rare, compared to Epitope A. Only a single monoclonal antibody to each epitope has been characterized to date, possibly reflecting immune suppression mechanisms that influence the antigenicity of these epitopes. The coordinates of Epitope G are unknown but like Epitope E, are nearby and/or overlapping with Epitope F. Mutation in the breathing core and temperature sensitivity of antibody blockade indicate that antibody access to Epitopes E, F, and G is mediated at the global particle level. The observation that exchange of both Epitope E and F residues from 2002 into 581 (581.2002E/F), but not E alone, was necessary to restore GII.4E binding, indicates that antibody access is also mediated at the local level by the conformation of surrounding residues. These conformation-dependent regulatory mechanisms are likely to extend to other epitopes within the P1 subdomain. Additional human monoclonal antibodies resulting from norovirus infection and vaccination are needed to identify other epitope signatures and the interdependence of distinct epitopes within a continuous antigen.

These studies expand our understanding of the complex mechanisms of human NoV immune evasion (FIG. 7) and persistence in human populations. In addition to immune-driven selective pressure on a subset of residues to change (antigenic drift); global particle structure (mediated by the distant breathing core residues) and local particle structure (mediated by closely surrounding residues) impact antibody access to blockade epitopes. These topological changes effectively reduce antibody binding without requiring changes in the residues that comprise the actual epitopes. These structure conformation-based immune evasion strategies are particularly advantageous for protecting essential conserved motifs that could be targeted by antibody. Norovirus joins other successful human pathogens such HIV, Influenza virus, Ebola virus, West Nile virus, and poliovirus that use conformation-based shielding of key essential residues to evade development of protective immunity. Further study is needed to test the effect of breathing core mutations on presentation of Epitopes E, F, and G. Concurrently to modifying the breathing core to change epitope access, surface residues that sterically block antibody access to the occluded epitopes may be identified. Change of these surface residues may be an easier path to designing a VLP immunogen with preferential presentation of conserved epitopes and better cross-reactivity with emergent GII.4 strains, a primary goal for NoV vaccinology. These concepts that characterize how viral particle dynamics influence antigen presentation and antibody access to blockade epitopes may be applicable to vaccine strategies to other highly penetrant, antigenically diverse viruses.

Virus-like particles. Synthetically derived (Bio Basic INC, Amherst, N.Y.) ORF2 genes were inserted directly into the VEE replicon vector. VLPs were expressed in Baby Hamster Kidney cells (ATCC CCL-10TM) and purified by velocity sedimentation in sucrose. VLP protein concentrations were determined by the BCA Protein Assay (Pierce, Rockford, Ill.). Uranyl acetate stained VLPs were visualized by transmission electron microscopy.

Enzyme Immunoassay (EIA). EIA plates were coated with 0.25 µg/ml VLP in PBS for 4 hours and blocked over night at 4° C. in 5% dry milk in PBS-0.05% Tween-20 before the addition of decreasing two-fold serial dilutions of mAb. Bound mAb was detected by anti-human/mouse IgG-HRP (GE Healthcare) and color developed with 1-Step Ultra TMB ELISA HRP substrate solution (Thermo-Fisher). Each step was followed by washing with PBS-0.05% Tween 20 and all reagents were diluted in 5% dry milk in PBS-0.05% Tween-20. All incubations were done at 37° C. To determine $EC_{50}$ values for antibodies with OD≥3× background at 2 µg/ml, EIA data were log transformed and fit using sigmoidal dose response analysis of non-linear data in GraphPad Prism 7.02 (graphpad.com). Monoclonal Abs below the limit of detection were assigned an $EC_{50}$ of 2× the assay upper limit of detection for statistical comparison. $EC_{50}$ values between VLPs were compared using the one-way ANOVA with Dunnett's posttest. A difference was considered significant if the P value was <0.05. $B_{max}$ and $K_D$ values were estimated by one-site specific binding non-linear curve fit of Mean OD values in GraphPad Prism 7.02.

Antibody blockade of VLP binding assay (Blockade). VLPs (0.25 µg/ml) were pretreated with decreasing concentrations of mAb for 1 h and added to pig gastric mucin type III (Sigma Aldrich, St. Louis, Mo.) coated plates for 1 h. Bound VLP was detected as described above using anti-VLP rabbit hyperimmune sera. Percent control binding is defined as the binding in the presence of antibody pretreatment compared to the binding in the absence multiplied by 100. The blockade data were fit using sigmoidal dose-response analysis of nonlinear data in GraphPad Prism 702. $EC_{50}$ and Hill slope values were calculated for antibodies that demonstrated blockade of at least 50% at the dilution series tested. Antibodies that did not block 50% of binding at the highest dilution tested were assigned an $EC_{50}$ of 2 times the assay upper limit of detection for statistical comparison.

Structural Modeling. Structural homology models representing the capsid P domain of GII.4.2006A (GenBank Accession Number EF126964.1) and immunocompromised patient virus Days 262 and 581 were generated using Swiss-Model. To do this, capsid amino acid sequences for these viruses were uploaded into the modeling server (swissmodel.expasy.org/interactive) and the appropriate background template was chosen by clicking "search for templates" and then choosing the known structure with the highest homology score. For all sequences, the chosen template was PDB accession number 3SLD, which is the crystal structure for the GII.4.2004 capsid bound to A trisaccharide. Models of the capsid dimers were created using the 3SLD template and downloaded in .pdb format. Models were rendered using MacPymol version 1.8.0.4 (pymol.org/). Hydrogen bonds were identified among specific amino acids by selecting those amino acids and using the "Action" command to choose "find", then "polar contacts", and then "within selection". The distance in angstroms between Epitopes E and F was calculated using Pymol's measurement tool. The low end of the range was determined by measuring the distance between the closest residues within each epitope, and the high end of the range was the distance between the furthest residues within each epitope.

Example 2

Figure 11A:
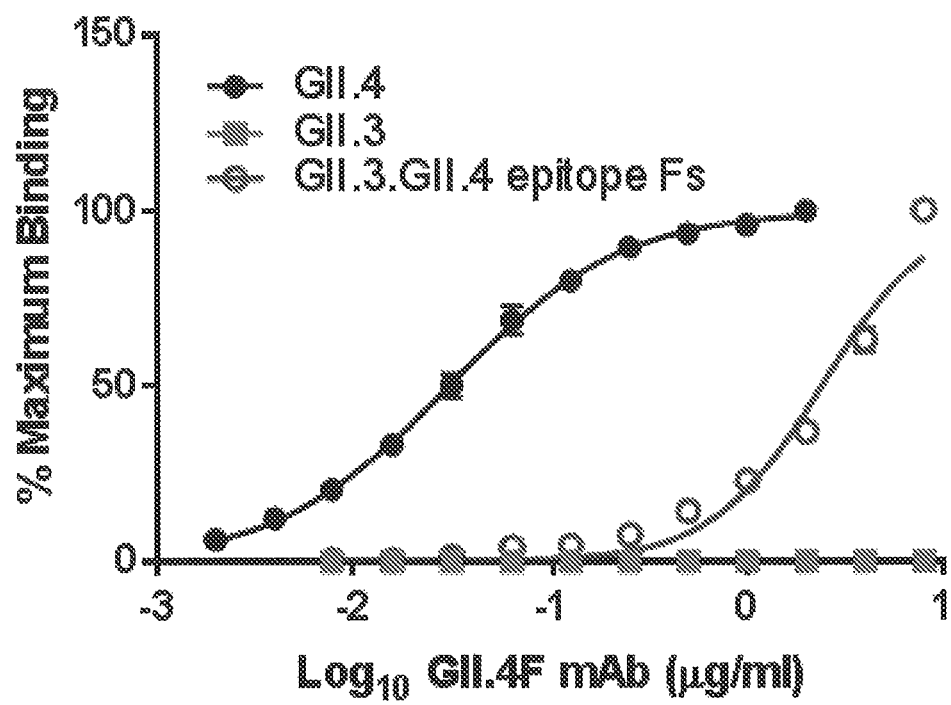
FIGS. 11A-11B: Broadening of blockade antibody response by transfer of epitope Fs of GII.4 into a GII.3 backbone. Introduction of conserved epitope Fs residues (GII.4 V327/V404) from GII.4 into GII.3 gains binding of GII.4Fs mAb (NVB 71.4) (FIG. 11A) and improves serum blockade Ab titer compared to GII.3 (FIG. 11B). *Significantly different from GII.3.GII.4Fs.
Figure 11B:
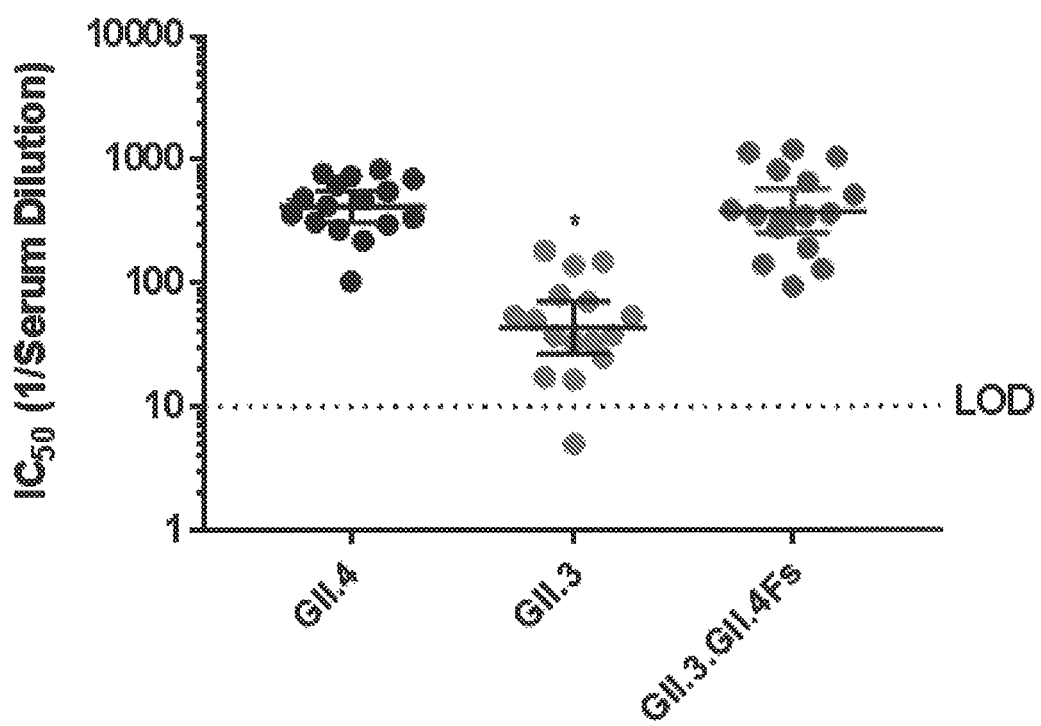

Additional data demonstrate broadening of antibody response by transfer of Epitope Fs of GII.4 (GII.4 residues V327/V404) into a GII.3 backbone. Residues 327/404 of Epitope Fs are the key residues needed for antibody binding. Previously we had defined Epitope F as residues 310, 316, 484, 493 (the NERK motif). These latter residues regulate antibody access to epitope Fs, not the binding site of antibody to epitope Fs (FIG. 11).

Example 3

Residues 393 and 396 anchor opposite ends of the loop of Epitope D. These residues vary between pandemic strains GII.4 2009 and 2012 and changes correspond to loss of blockade potency for Epitope D monoclonal antibodies NVB 97 and NO66. GII.4 2012 VLPs with GII.4 2009 Epitope D substitutions were developed to dissect the role of residues 393 and 396 in binding of Epitope D antibodies. GII.4.2012.09D (residues 393-396) and GII.4 2012.H396P improved the $EC_{50}$ for NO66 binding more than 10-fold compared to GII.4 2012, identifying residue 396 as an anchor for NO66 and extending Epitope D. GII.4 2012.G393S restored NVB 97 binding but GII.4.2012.09D and GII.4 2012.H396P did not, indicating that the P396 may negatively impact NVB 97 binding to epitope D (FIG. 12).

While there are shown and described particular embodiments of the invention, it is to be understood that the invention is not limited thereto but may be otherwise variously embodied and practiced within the scope of the following claims. Since numerous modifications and alternative embodiments of the present invention will be readily apparent to those skilled in the art, this description is to be construed as illustrative only and is for the purpose of teaching those skilled in the art the best mode for carrying out the present invention. Accordingly, all suitable modifications and equivalents may be considered to fall within the scope of the following claims.

TABLE 1

Characteristics of monoclonal antibodies used in this study

| mAb | Synonyms | Species | Immunogen | Epitope |
| --- | --- | --- | --- | --- |
| GII.4E | GII.4.2002.G6 | Mouse | GII.4.2002 | Variable, Blockade, Epitope E of GII.4.2002 |
| GII.4F | NVB 71.4 | Human | Natural Infection | Conserved GII.4, Blockade, Conformation-Dependent, Epitope F |
| GII.4G | GII.4.2002.G5 MAB227P | Mouse | GII.4.2002 | Conserved GII.4, Blockade, Conformation-Dependent, Epitope G |

That which is claimed is:

1. A chimeric norovirus capsid protein consisting of a norovirus VP1 major capsid protein backbone from norovirus strain GII.4.1974 (SEQ ID NO:1), norovirus strain GII.4.1987 (SEQ ID NO:2), norovirus strain GII.4.1997 (SEQ ID NO:3), norovirus strain GII.4.2002 (SEQ ID NO:4), norovirus strain GII.4.2002a (SEQ ID NO:5), norovirus strain GII.4.2004 (SEQ ID NO:6), norovirus strain GII.4.2005 (SEQ ID NO:7), norovirus strain GII.4.2006 (SEQ ID NO:8), norovirus strain GII.4.2007 (SEQ ID NO:9), norovirus strain GII.4.2008a (SEQ ID NO:10), norovirus strain GII.4.2008s (SEQ ID NO:11), norovirus strain GII.4.2009 (SEQ ID NO:12), or norovirus strain GII.4.2012 (SEQ ID NO:13) in which two or more sets of amino acid residues are substituted into the capsid protein backbone to introduce at least one epitope from each of two or more different norovirus strains of the above norovirus strains, each of which is different from one another and each of which is different from the norovirus strain of the capsid protein backbone, wherein at least one of the two or more sets of amino acid residues comprises any one of the following sets of amino acid residues (a)-(f) in any combination:

a) amino acid residues 391, 393, 394, 395 and 396 (Epitope D);

b) amino acid residues 234, 310, 316, 484 and 493 (Epitope F); and
c) amino acid residues 327 and 404 (Epitope Fs),
wherein amino acid residue numbering of (a)-(c) is based on the amino acid sequence of any of SEQ ID NOs:4-13; and
d) amino acid residues 391, 393, 394 and 395 (Epitope D);
e) amino acid residues 234, 310, 316, 483 and 492 (Epitope F), and
f) amino acid residues 327 and 403 (Epitope Fs),
wherein amino acid residue numbering of (d)-(f) is based on the amino acid sequence of SEQ ID NOs:1-3.

2. A chimeric norovirus capsid protein consisting of a norovirus VP1 major capsid protein backbone from norovirus strain GII.4.1974 (SEQ ID NO:1), norovirus strain GII.4.1987 (SEQ ID NO:2), norovirus strain GII.4.1997 (SEQ ID NO:3), norovirus strain GII.4.2002 (SEQ ID NO:4), norovirus strain GII.4.2002a (SEQ ID NO:5), norovirus strain GII.4.2004 (SEQ ID NO:6), norovirus strain GII.4.2005 (SEQ ID NO:7), norovirus strain GII.4.2006 (SEQ ID NO:8), norovirus strain GII.4.2007 (SEQ ID NO:9), norovirus strain GII.4.2008a (SEQ ID NO:10), norovirus strain GII.4.2008s (SEQ ID NO:11), norovirus strain GII.4.2009 (SEQ ID NO:12), or norovirus strain GII.4.2012 (SEQ ID NO:13),
in which amino acid residues 234, 310, 316, 484 and 493 (Epitope F) are substituted into the capsid protein backbone, wherein amino acid residue numbering is based on the amino acid sequence of any of SEQ ID NOs:4-13, or
in which amino acid residues 234, 310, 316, 483 and 492 (Epitope F) are substituted into the capsid protein backbone, wherein amino acid residue numbering is based on the amino acid sequence of any of SEQ ID NOs:1-3, thereby introducing Epitope F from a norovirus strain that is different from the norovirus strain of the capsid protein backbone.

3. The chimeric norovirus capsid protein of claim 2, in which one or more of the following sets of amino acid residues (a)-(i):
a) amino acid residues 294, 296, 297, 298, 368 and 372 (Epitope A);
b) amino acid residues 333 and 382 (Epitope B);
c) amino acid residues 340 and 376 (Epitope C);
d) amino acid residues 391, 393, 394, 395 and 396 (Epitope D);
e) amino acid residues 407, 412 and 413 (Epitope E); and
f) amino acid residues 327 and 404 (Epitope Fs),
wherein amino acid residue numbering of (a)-(f) is based on the amino acid sequence of any of SEQ ID NOs:4-13, and
g) amino acid residues 391, 393, 394 and 395 (Epitope D);
h) amino acid residues 406, 411 and 412 (Epitope E); and
i) amino acid residues 327 and 403 (Epitope Fs),
wherein amino acid residue numbering of (g)-(i) is based on the amino acid sequence of SEQ ID NOs:1-3,
are substituted into the capsid protein backbone to introduce at least one epitope from a norovirus strain that is different from the norovirus strain of Epitope F and different from the strain of the capsid protein backbone.

4. A chimeric norovirus capsid protein consisting of a norovirus VP1 major capsid protein backbone from norovirus strain GII.3 (SEQ ID NO:14), in which one or more, in any combination, of the following sets of amino acid residues (a)-(k) are substituted into the norovirus capsid protein backbone to introduce one or more epitope in any combination, from one or more different norovirus strains, in any combination, as follows:

a) amino acid residues 294, 296, 297, 298, 368 and 372 (Epitope A) of a norovirus strain having the amino acid sequence of any one of SEQ ID NO:4-13, substituted at positions 294, 310, 311, 312, 381 and 384, respectively, in the amino acid sequence of SEQ ID NO:14;
b) amino acid residues 333 and 382 (Epitope B) of a norovirus strain having the amino acid sequence of any one of SEQ ID NO:4-13, substituted at positions 347 and 394, respectively, in the amino acid sequence of SEQ ID NO:14;
c) amino acid residues 340 and 376 (Epitope C) of a norovirus strain having the amino acid sequence of any one of SEQ ID NO:4-13, substituted at positions 353 and 388, respectively, in the amino acid sequence of SEQ ID NO:14;
d) amino acid residues 391, 393, 394 and 395 (Epitope D) of a norovirus strain having the amino acid sequence of any one of SEQ ID NO:4-13, substituted at positions 403, 404, 405 and 406, respectively, in the amino acid sequence of SEQ ID NO:14;
e) amino acid residues 407, 412 and 413 (Epitope E) of a norovirus strain having the amino acid sequence of any one of SEQ ID NO:4-13, substituted at positions 415, 420 and 421, respectively, in the amino acid sequence of SEQ ID NO:14;
f) amino acid residues 234, 310, 316, 484 and 493 (Epitope F) of a norovirus strain having the amino acid sequence of any one of SEQ ID NO:4-13, substituted at positions 234, 324, 330, 492 and 501, respectively, in the amino acid sequence of SEQ ID NO:14; and
g) amino acid residues 327 and 404 (Epitope Fs) of a norovirus strain having the amino acid sequence of any one of SEQ ID NO:4-13, substituted at positions 341 and 412, respectively, in the amino acid sequence of SEQ ID NO:14; and
h) amino acid residues 391, 393, 394 and 395 (Epitope D) of a norovirus strain having the amino acid sequence of any one of SEQ ID NO:1-3, substituted at positions 403, 404, 405 and 406, respectively, in the amino acid sequence of SEQ ID NO:14;
i) amino acid residues 406, 411 and 412 (Epitope E) of a norovirus strain having the amino acid sequence of any one of SEQ ID NO:1-3, substituted at positions 415, 420 and 421, respectively, in the amino acid sequence of SEQ ID NO:14;
j) amino acid residues 234, 310, 316, 483 and 492 (Epitope F) of a norovirus strain having the amino acid sequence of any one of SEQ ID NO:1-3, substituted at positions 234, 324, 330, 492 and 501, respectively, in the amino acid sequence of SEQ ID NO:14, and
k) amino acid residues 327 and 403 (Epitope Fs) of a norovirus strain having the amino acid sequence of any one of SEQ ID NO:1-3, substituted at positions 341 and 412, respectively, in the amino acid sequence of SEQ ID NO:14.

5. An isolated nucleic acid molecule encoding the chimeric norovirus capsid protein of claim 1.

6. A vector comprising the nucleic acid molecule of claim 5.

7. A Venezuelan Equine Encephalitis (VEE) replicon particle (VRP) comprising the nucleic acid molecule of claim 5.

8. A virus like particle (VLP) comprising the chimeric norovirus capsid protein of claim 1.

9. A composition comprising the chimeric norovirus capsid protein of claim 1 in a pharmaceutically acceptable carrier.

10. A method of producing an immune response to a norovirus in a subject, comprising administering to the subject an effective amount of the chimeric norovirus capsid protein of claim 1.

11. A method of treating a norovirus infection in a subject in need thereof, comprising administering to the subject an effective amount of the chimeric norovirus capsid protein of claim 1.

12. A method of preventing a disorder associated with norovirus infection in a subject, comprising administering to the subject an effective amount of the chimeric norovirus capsid protein of claim 1.

13. A method of protecting a subject from the effects of norovirus infection, comprising administering to the subject an effective amount of the chimeric norovirus capsid protein of claim 1.

14. A method of detecting a neutralizing antibody to a norovirus, the method comprising determining whether an antibody binds to the chimeric norovirus capsid protein of claim 1, wherein binding by the antibody to the chimeric norovirus capsid protein indicates that the antibody is a neutralizing antibody to a norovirus.

15. A method of identifying a neutralizing antibody to a norovirus, comprising:
   (a) contacting an antibody with the chimeric norovirus capsid protein of claim 1; and
   (b) determining if the antibody binds to the chimeric norovirus capsid protein, wherein binding by the antibody to the chimeric norovirus capsid protein identifies the antibody as a neutralizing antibody to a norovirus.

16. A method of identifying an immunogenic composition that induces a neutralizing antibody to a norovirus in a subject, the method comprising:
   (a) contacting a biological sample from a subject that has been administered the immunogenic composition with the chimeric norovirus capsid protein of claim 1;
   (b) determining if the biological sample comprises an antibody that binds the chimeric norovirus capsid protein; and
   (c) identifying the immunogenic composition as inducing a neutralizing antibody to a norovirus in the subject if the biological sample comprises an antibody that binds to the chimeric norovirus capsid protein.

17. A method of identifying an immunogenic composition that induces a neutralizing antibody to a norovirus in a subject, the method comprising:
   (a) administering an immunogenic composition comprising a norovirus antigen to a subject in an amount effective to induce antibodies against the norovirus antigen;
   (b) contacting a biological sample from the subject with the chimeric norovirus capsid protein of claim 1;
   (c) determining if the biological sample comprises an antibody that binds the chimeric norovirus capsid protein; and
   (d) identifying the immunogenic composition as inducing a neutralizing antibody to a norovirus in the subject if the biological sample comprises an antibody that binds the chimeric norovirus capsid protein.

18. The isolated nucleic acid molecule of claim 5, wherein the nucleic acid molecule is an RNA molecule.

19. The chimeric norovirus capsid protein of claim 1, further comprising at least one of the following sets of amino acid residues (g)-(k), in any combination:
   g) amino acid residues 294, 296, 297, 298, 368 and 372 (Epitope A);
   h) amino acid residues 333 and 382 (Epitope B);
   i) amino acid residues 340 and 376 (Epitope C); and
   j) amino acid residues 407, 412 and 413 (Epitope E);
   wherein amino acid residue numbering of (g)-(j) is based on the amino acid sequence of any of SEQ ID NOs:4-13; and
   k) amino acid residues 406, 411 and 412 (Epitope E), wherein amino acid residue numbering is based on the amino acid sequence of SEQ ID NOs:1-3.

20. An isolated nucleic acid molecule encoding the chimeric norovirus capsid protein of claim 4.

21. A vector comprising the nucleic acid molecule of claim 20.

22. A Venezuelan Equine Encephalitis (VEE) replicon particle (VRP) comprising the nucleic acid molecule of claim 20.

23. A virus like particle (VLP) comprising the chimeric norovirus capsid protein of claim 4.

24. A composition comprising the chimeric norovirus capsid protein of claim 4 in a pharmaceutically acceptable carrier.

25. A method of producing an immune response to a norovirus in a subject, comprising administering to the subject an effective amount of the chimeric norovirus capsid protein of claim 4.

26. A method of treating a norovirus infection in a subject in need thereof, comprising administering to the subject an effective amount of the chimeric norovirus capsid protein of claim 4.

27. A method of preventing a disorder associated with norovirus infection in a subject, comprising administering to the subject an effective amount of the chimeric norovirus capsid protein of claim 4.

28. A method of protecting a subject from the effects of norovirus infection, comprising administering to the subject an effective amount of the chimeric norovirus capsid protein of claim 4.

29. A method of detecting a neutralizing antibody to a norovirus, the method comprising determining whether an antibody binds to the chimeric norovirus capsid protein of claim 4, wherein binding by the antibody to the chimeric norovirus capsid protein indicates that the antibody is a neutralizing antibody to a norovirus.

30. A method of identifying a neutralizing antibody to a norovirus, comprising:
   (a) contacting an antibody with the chimeric norovirus capsid protein of claim 4; and
   (b) determining if the antibody binds to the chimeric norovirus capsid protein, wherein binding by the antibody to the chimeric norovirus capsid protein identifies the antibody as a neutralizing antibody to a norovirus.

31. A method of identifying an immunogenic composition that induces a neutralizing antibody to a norovirus in a subject, the method comprising:
   (a) contacting a biological sample from a subject that has been administered the immunogenic composition with the chimeric norovirus capsid protein of claim 4;
   (b) determining if the biological sample comprises an antibody that binds the chimeric norovirus capsid protein; and
   (c) identifying the immunogenic composition as inducing a neutralizing antibody to a norovirus in the subject if the biological sample comprises an antibody that binds to the chimeric norovirus capsid protein.

32. A method of identifying an immunogenic composition that induces a neutralizing antibody to a norovirus in a subject, the method comprising:

(a) administering an immunogenic composition comprising a norovirus antigen to a subject in an amount effective to induce antibodies against the norovirus antigen;
(b) contacting a biological sample from the subject with the chimeric norovirus capsid protein of claim 4;
(c) determining if the biological sample comprises an antibody that binds the chimeric norovirus capsid protein; and
(d) identifying the immunogenic composition as inducing a neutralizing antibody to a norovirus in the subject if the biological sample comprises an antibody that binds the chimeric norovirus capsid protein.

33. The isolated nucleic acid molecule of claim 20, wherein the nucleic acid molecule is an RNA molecule.

* * * * *

SEQUENCE LISTING

```
<160> NUMBER OF SEQ ID NOS: 14

<210> SEQ ID NO 1
<211> LENGTH: 539
<212> TYPE: PRT
<213> ORGANISM: Norovirus Hu/GII.4/CHDC5191/1974/US

<400> SEQUENCE: 1

Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Ile Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ser Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ala His Asp Ser Thr Leu
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220
```

```
Lys Pro Phe Thr Val Pro Ile Leu Thr Val Glu Glu Met Ser Asn Ser
225                 230                 235                 240

Arg Phe Pro Ile Pro Leu Glu Lys Leu Tyr Thr Gly Pro Ser Ser Ala
            245                 250                 255

Phe Val Val Gln Pro Gln Asn Gly Arg Cys Thr Thr Asp Gly Val Leu
        260                 265                 270

Leu Gly Thr Thr Gln Leu Ser Ala Val Asn Ile Cys Asn Phe Arg Gly
        275                 280                 285

Asp Val Thr Arg Val Gly Ile Ser His Asp Tyr Thr Met Asn Leu Val
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Leu Leu Thr Gln
            325                 330                 335

Thr Thr Arg Ala Asp Gly Ser Thr Arg Ala His Lys Ala Thr Val Ser
        340                 345                 350

Thr Gly Ser Val His Phe Thr Pro Lys Leu Gly Ser Val Gln Phe Thr
        355                 360                 365

Thr Asp Thr Asn Asn Asp Phe Gln Thr Gly Gln Asn Thr Lys Phe Thr
    370                 375                 380

Pro Val Gly Val Ile Gln Asp Gly Asp His His Gln Asn Glu Pro Gln
385                 390                 395                 400

Gln Trp Val Leu Pro Asn Tyr Ser Gly Thr Ser Gly His Asn Val His
            405                 410                 415

Leu Ala Pro Ala Val Ala Pro Thr Phe Pro Gly Glu Gln Leu Leu Phe
        420                 425                 430

Phe Arg Ser Thr Met Pro Gly Cys Ser Gly Tyr Pro Asn Met Asn Leu
        435                 440                 445

Asp Cys Leu Leu Pro Gln Glu Trp Val Leu His Phe Tyr Gln Glu Ala
    450                 455                 460

Ala Pro Ala Gln Ser Asp Val Ala Leu Leu Arg Phe Val Asn Pro Asp
465                 470                 475                 480

Thr Gly Arg Val Leu Phe Glu Cys Lys Leu His Lys Ser Gly Tyr Ile
            485                 490                 495

Thr Val Ala His Thr Gly Pro Tyr Asp Leu Val Ile Pro Pro Asn Gly
        500                 505                 510

Tyr Phe Arg Phe Asp Ser Trp Val Asn Gln Phe Tyr Thr Leu Ala Pro
        515                 520                 525

Met Gly Asn Gly Thr Gly Arg Arg Arg Ala Leu
    530                 535

<210> SEQ ID NO 2
<211> LENGTH: 539
<212> TYPE: PRT
<213> ORGANISM: Human calicivirus Hu/NL

```
Thr Val Ser Pro Arg Asn Ala Pro Gly Glu Ile Leu Trp Ser Ala Pro
 65                  70                  75                  80

Leu Gly Pro Asp Leu Asn Pro Tyr Leu Ser His Leu Ser Arg Met Tyr
                 85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser His Asp Ser Thr Leu
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Ser Asn Ser
225                 230                 235                 240

Arg Phe Pro Ile Pro Leu Glu Lys Leu Tyr Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Ala Val Asn Ile Cys Asn Phe Arg Gly
        275                 280                 285

Asp Val Thr His Ile Val Gly Ser His Asp Tyr Thr Met Asn Leu Ala
    290                 295                 300

Ser Gln Asn Trp Ser Asn Tyr Asp Pro Thr Glu Glu Ile Pro Ala Pro
305                 310                 315                 320

Leu Gly Thr Pro Asp Phe Val Gly Lys Ile Gln Gly Leu Leu Thr Gln
                325                 330                 335

Thr Thr Arg Ala Asp Gly Ser Thr Arg Ala His Lys Ala Thr Val Ser
            340                 345                 350

Thr Gly Ser Val His Phe Thr Pro Lys Leu Gly Ser Val Gln Phe Thr
        355                 360                 365

Thr Asp Thr Asn Asn Asp Phe Gln Thr Gly Gln Asn Thr Lys Phe Thr
    370                 375                 380

Pro Val Gly Val Ile Gln Asp Gly Asp His His Gln Asn Glu Pro Gln
385                 390                 395                 400

Gln Trp Val Leu Pro Asn Tyr Ser Gly Arg Thr Gly His Asn Val His
                405                 410                 415

Leu Ala Pro Ala Val Ala Pro Thr Phe Pro Gly Glu Gln Leu Leu Phe
            420                 425                 430

Phe Arg Ser Thr Met Pro Gly Cys Ser Gly Tyr Pro Asn Met Asn Leu
        435                 440                 445

Asp Cys Leu Leu Pro Gln Glu Trp Val Leu His Phe Tyr Gln Glu Ala
    450                 455                 460

Ala Pro Ala Gln Ser Asp Val Ala Leu Leu Arg Phe Val Asn Pro Asp
465                 470                 475                 480
```

```
Thr Gly Arg Val Leu Phe Glu Cys Lys Leu His Lys Ser Gly Tyr Ile
            485                 490                 495
Thr Val Ala His Thr Gly Pro Tyr Asp Leu Val Ile Pro Pro Asn Gly
            500                 505                 510
Tyr Phe Arg Phe Asp Ser Trp Val Asn Gln Phe Tyr Thr Leu Ala Pro
            515                 520                 525
Met Gly Asn Gly Thr Gly Arg Arg Ala Leu
            530                 535

<210> SEQ ID NO 3
<211> LENGTH: 539
<212> TYPE: PRT
<213> ORGANISM: Norovirus Hu/GII.4/1997/USA

<400> SEQUENCE: 3

Met Lys Met Ala Ser Asn Asp Ala Ser Pro Ser Asp Gly Ser Thr Ala
1               5                   10                  15
Asn Leu Val Pro Glu Val Asn Asn Glu Val Met Ala Leu Glu Pro Val
            20                  25                  30
Val Gly Ala Ala Ile Ala Ala Pro Val Ala Gly Gln Gln Asn Val Ile
            35                  40                  45
Asp Pro Trp Ile Arg Asn Asn Phe Val Gln Ala Pro Gly Gly Glu Phe
        50                  55                  60
Thr Val Ser Pro Arg Asn Ala Pro Gly Glu Ile Leu Trp Ser Ala Pro
65                  70                  75                  80
Leu Gly Pro Asp Leu Asn Pro Tyr Leu Ser His Leu Ala Arg Met Tyr
                85                  90                  95
Asn Gly Tyr Ala Gly Gly Phe Glu Val Gln Val Ile Leu Ala Gly Asn
            100                 105                 110
Ala Phe Thr Ala Gly Lys Ile Ile Phe Ala Ala Val Pro Pro Asn Phe
            115                 120                 125
Pro Thr Glu Gly Leu Ser Pro Ser Gln Val Thr Met Phe Pro His Ile
            130                 135                 140
Ile Val Asp Val Arg Gln Leu Glu Pro Val Leu Ile Pro Leu Pro Asp
145                 150                 155                 160
Val Arg Asn Asn Phe Tyr His Tyr Asn Gln Ser Asn Asp Ser Thr Ile
                165                 170                 175
Lys Leu Ile Ala Met Leu Tyr Thr Pro Leu Arg Ala Asn Asn Ala Gly
            180                 185                 190
Asp Asp Val Phe Thr Val Ser Cys Arg Val Leu Thr Arg Pro Ser Pro
            195                 200                 205
Asp Phe Asp Phe Ile Phe Leu Val Pro Pro Thr Val Glu Ser Arg Thr
            210                 215                 220
Lys Pro Phe Thr Val Pro Ile Leu Thr Val Glu Met Ser Asn Ser Arg
225                 230                 235                 240
Arg Phe Pro Ile Pro Leu Glu Lys Leu Tyr Thr Gly Pro Ser Ser Ala
                245                 250                 255
Phe Val Val Gln Pro Gln Asn Gly Arg Cys Thr Thr Asp Gly Val Leu
            260                 265                 270
Leu Gly Thr Thr Gln Leu Ser Ala Val Asn Ile Cys Thr Phe Arg Gly
            275                 280                 285
Asp Ile Thr His Ile Ala Gly Ser His Asp Tyr Thr Met Asn Leu Ala
            290                 295                 300
Ser Gln Asn Trp Ser Asn Tyr Asp Pro Thr Glu Glu Ile Pro Ala Pro
305                 310                 315                 320
```

-continued

```
Leu Gly Thr Pro Asp Phe Val Gly Lys Ile Gln Gly Met Leu Thr Gln
            325                 330                 335

Thr Thr Arg Glu Asp Gly Ser Thr Arg Ala His Lys Ala Thr Val Ser
        340                 345                 350

Thr Gly Ser Val His Phe Thr Pro Lys Leu Gly Ser Val Gln Tyr Thr
    355                 360                 365

Thr Asp Thr Asn Asn Asp Phe Gln Thr Gly Gln Asn Thr Lys Phe Thr
370                 375                 380

Pro Val Gly Val Ile Gln Asp Gly Gly Asn His Gln Asn Glu Pro Gln
385                 390                 395                 400

Gln Trp Val Leu Pro Asn Tyr Ser Gly Arg Thr Gly His Asn Val His
                405                 410                 415

Leu Ala Pro Ala Val Ala Pro Thr Phe Pro Gly Glu Gln Leu Leu Phe
            420                 425                 430

Phe Arg Ser Thr Met Pro Gly Cys Ser Gly Tyr Pro Asn Met Asn Leu
        435                 440                 445

Asp Cys Leu Leu Pro Gln Glu Trp Val Gln His Phe Tyr Gln Glu Ala
    450                 455                 460

Ala Pro Ala Gln Ser Asp Val Ala Leu Leu Arg Phe Val Asn Pro Asp
465                 470                 475                 480

Thr Gly Arg Val Leu Phe Glu Cys Lys Leu His Lys Ser Gly Tyr Val
                485                 490                 495

Thr Val Ala His Thr Gly Pro His Asp Leu Val Ile Pro Pro Asn Gly
            500                 505                 510

Tyr Phe Arg Phe Asp Ser Trp Val Asn Gln Phe Tyr Thr Leu Ala Pro
        515                 520                 525

Met Gly Asn Gly Ala Gly Arg Arg Arg Ala Leu
    530                 535
```

<210> SEQ ID NO 4
<211> LENGTH: 540
<212> TYPE: PRT
<213> ORGANISM: Norovirus Hu/GII.4.2004/Farmington Hills

<400> SEQUENCE: 4

```
Met Lys Met Ala Ser Asn Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160
```

```
Val Arg Asn Asn Phe Tyr His Tyr Asn Gln Ser Asn Asp Pro Thr Ile
                165                 170                 175
Lys Leu Ile Ala Met Leu Tyr Thr Pro Leu Arg Ala Asn Asn Ala Gly
            180                 185                 190
Glu Asp Val Phe Thr Val Ser Cys Arg Val Leu Thr Arg Pro Ser Pro
        195                 200                 205
Asp Phe Asp Phe Ile Phe Leu Val Pro Pro Thr Val Glu Ser Arg Thr
    210                 215                 220
Lys Pro Phe Thr Val Pro Ile Leu Thr Val Glu Met Thr Asn Ser
225                 230                 235                 240
Arg Phe Pro Ile Pro Leu Glu Lys Leu Phe Thr Gly Pro Ser Gly Ala
                245                 250                 255
Phe Val Val Gln Pro Gln Asn Gly Arg Cys Thr Thr Asp Gly Val Leu
            260                 265                 270
Leu Gly Thr Thr Gln Leu Ser Pro Val Asn Ile Cys Thr Phe Arg Gly
        275                 280                 285
Asp Val Thr His Ile Ala Gly Thr His Asn Tyr Thr Met Asn Leu Ala
    290                 295                 300
Ser Gln Asn Trp Asn Asn Tyr Asp Pro Thr Glu Glu Ile Pro Ala Pro
305                 310                 315                 320
Leu Gly Thr Pro Asp Phe Val Gly Arg Ile Gln Gly Met Leu Thr Gln
                325                 330                 335
Thr Thr Arg Gly Asp Gly Ser Thr Arg Gly His Lys Ala Thr Val Ser
            340                 345                 350
Thr Gly Asp Val His Phe Thr Pro Lys Leu Gly Ser Ile Gln Phe Asn
        355                 360                 365
Thr Asp Thr Asn Asn Asp Phe Glu Thr Gly Gln Asn Thr Lys Phe Thr
    370                 375                 380
Pro Val Gly Val Val Gln Asp Gly Asn Gly Ala His Gln Asn Glu Pro
385                 390                 395                 400
Gln Gln Trp Val Leu Pro Ser Tyr Ser Gly Arg Thr Gly His Asn Val
                405                 410                 415
His Leu Ala Pro Ala Val Ala Pro Thr Phe Pro Gly Glu Gln Leu Leu
            420                 425                 430
Phe Phe Arg Ser Thr Met Pro Gly Cys Ser Gly Tyr Pro Asn Met Asn
        435                 440                 445
Leu Asp Cys Leu Leu Pro Gln Glu Trp Val Gln His Phe Tyr Gln Glu
    450                 455                 460
Ala Ala Pro Ala Gln Ser Asp Val Ala Leu Leu Arg Phe Val Asn Pro
465                 470                 475                 480
Asp Thr Gly Arg Val Leu Phe Glu Cys Lys Leu His Lys Ser Gly Tyr
                485                 490                 495
Val Thr Val Ala His Thr Gly Gln His Asp Leu Val Ile Pro Pro Asn
            500                 505                 510
Gly Tyr Phe Arg Phe Asp Ser Trp Val Asn Gln Phe Tyr Thr Leu Ala
        515                 520                 525
Pro Met Gly Asn Gly Thr Gly Arg Arg Arg Ala Leu
530                 535                 540

<210> SEQ ID NO 5
<211> LENGTH: 540
<212> TYPE: PRT
<213> ORGANISM: Norovirus GII.4.2002a
```

<400> SEQUENCE: 5

```
Met Lys Met Ala Ser Asn Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
            85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
            165                 170                 175

Lys Leu Ile Ala Met Leu Tyr Thr Pro Leu Arg Ala Asn Asn Ala Gly
            180                 185                 190

Glu Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Ser Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
            245                 250                 255

Phe Val Val Gln Pro Gln Asn Gly Arg Cys Thr Thr Asp Gly Val Leu
        260                 265                 270

Leu Gly Thr Thr Gln Leu Ser Pro Val Asn Ile Cys Thr Phe Arg Gly
    275                 280                 285

Asp Val Thr His Ile Ala Gly Thr His Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Arg Ile Gln Gly Met Leu Thr Gln
            325                 330                 335

Thr Thr Arg Gly Asp Gly Ser Thr Arg Gly His Lys Ala Thr Val Ser
            340                 345                 350

Thr Gly Asp Val His Phe Thr Pro Lys Leu Gly Ser Ile Gln Phe Asn
        355                 360                 365

Thr Asp Thr Asn Asn Asp Phe Glu Thr Gly Gln Asn Thr Lys Phe Thr
    370                 375                 380

Pro Val Gly Val Val Gln Asp Gly Asn Gly Thr His Gln Asn Glu Pro
385                 390                 395                 400

Gln Gln Trp Val Leu Pro Ser Tyr Ser Gly Arg Thr Gly His Asn Val
            405                 410                 415
```

His Leu Ala Pro Ala Val Ala Pro Thr Phe Pro Gly Glu Gln Leu Leu
                420                 425                 430

Phe Phe Arg Ser Thr Met Pro Gly Cys Ser Gly Tyr Pro Asn Met Asn
            435                 440                 445

Leu Asp Cys Leu Leu Pro Gln Glu Trp Val Gln His Phe Tyr Gln Glu
        450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
        530                 535                 540

<210> SEQ ID NO 6
<211> LENGTH: 540
<212> TYPE: PRT
<213> ORGANISM: Norovirus Hu/GII.4/Hunter 284E/040/AU

<400> SEQUENCE: 6

Met Lys Met Ala Ser Asn Asp Ala Thr Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Val Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Leu Tyr His Tyr Asn Gln Ser Asn Asp Pro Thr Ile
                165                 170                 175

Arg Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Met Phe Leu Val Pro Pro Thr Val Glu Ser Arg Thr
    210                 215                 220

Lys Pro Phe Ser Val Pro Ile Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

```
Phe Val Val Gln Pro Gln Asn Gly Arg Cys Thr Thr Asp Gly Val Leu
                260                 265                 270

Leu Gly Thr Thr Gln Leu Ser Pro Val Asn Ile Cys Thr Phe Arg Gly
            275                 280                 285

Asp Val Thr His Ile Ala Gly Ala Gln Asn Tyr Thr Met Asn Leu Ala
        290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Arg Asp Gly Ser Thr Arg Gly His Lys Ala Thr Val Ser
            340                 345                 350

Thr Gly Ser Val His Phe Thr Pro Lys Leu Gly Ser Val Gln Phe Ser
        355                 360                 365

Thr Asp Thr Ser Asn Asp Phe Glu Thr Gly Gln Asn Thr Arg Phe Thr
370                 375                 380

Pro Val Gly Val Val Gln Asp Gly Ser Thr Thr His Gln Asn Glu Pro
385                 390                 395                 400

Gln Gln Trp Val Leu Pro Asp Tyr Ser Gly Arg Asp Ser His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asn
        435                 440                 445

Leu Asp Cys Leu Leu Pro Gln Glu Trp Val Gln His Phe Tyr Gln Glu
450                 455                 460

Ser Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Ile Asn Gln Phe Tyr Thr Leu Ala
        515                 520                 525

Pro Met Gly Asn Gly Ala Gly Arg Arg Arg Ala Leu
530                 535                 540

<210> SEQ ID NO 7
<211> LENGTH: 540
<212> TYPE: PRT
<213> ORGANISM: Norovirus Hu/Sakai/04-179/2005/JP

<400> SEQUENCE: 7

Met Lys Met Ala Ser Asn Asp Ala Ser Pro Ser Asp Gly Ser Thr Ala
1               5                   10                  15

Asn Leu Val Pro Glu Val Asn Asn Glu Val Met Ala Leu Glu Pro Val
                20                  25                  30

Val Gly Ala Ala Ile Ala Ala Pro Val Ala Gly Gln Gln Asn Val Ile
            35                  40                  45

Asp Pro Trp Ile Arg Asn Asn Phe Val Gln Ala Pro Gly Gly Glu Phe
        50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95
```

```
Asn Gly Tyr Ala Gly Gly Phe Glu Val Gln Val Ile Leu Ala Gly Asn
            100                 105                 110
Ala Phe Thr Ala Gly Lys Ile Ile Phe Ala Ala Val Pro Pro Asn Phe
        115                 120                 125
Pro Thr Glu Gly Leu Ser Pro Ser Gln Val Thr Met Phe Pro His Ile
    130                 135                 140
Ile Val Asp Val Arg Gln Leu Glu Pro Val Leu Ile Pro Leu Pro Asp
145                 150                 155                 160
Val Arg Asn Asn Phe Tyr His Tyr Asn Gln Ser Asn Asp Ser Thr Ile
                165                 170                 175
Lys Leu Ile Ala Met Leu Tyr Thr Pro Leu Arg Ala Asn Asn Ala Gly
            180                 185                 190
Asp Asp Val Phe Thr Val Ser Cys Arg Val Leu Thr Arg Pro Ser Pro
        195                 200                 205
Asp Phe Asp Phe Ile Phe Leu Val Pro Pro Thr Val Glu Ser Arg Thr
    210                 215                 220
Lys Pro Phe Thr Val Pro Ile Leu Thr Val Glu Glu Met Thr Asn Ser
225                 230                 235                 240
Arg Phe Pro Ile Pro Leu Glu Lys Leu Phe Thr Gly Pro Ser Ser Ala
                245                 250                 255
Phe Val Val Gln Pro Gln Asn Gly Arg Cys Thr Thr Asp Gly Val Leu
            260                 265                 270
Leu Gly Thr Thr Gln Leu Ser Pro Val Asn Ile Cys Thr Phe Arg Gly
        275                 280                 285
Asp Val Thr His Ile Pro Gly Thr Arg Thr Tyr Arg Met Asn Leu Ala
    290                 295                 300
Ser Gln Asn Trp Asn Asn Tyr Asp Pro Thr Glu Glu Ile Pro Ala Pro
305                 310                 315                 320
Leu Gly Thr Pro Asp Phe Val Gly Lys Ile Gln Gly Met Leu Thr Gln
                325                 330                 335
Thr Thr Lys Gly Asp Gly Ser Thr Arg Gly His Lys Ala Thr Val Ser
            340                 345                 350
Thr Gly Ser Val Asp Phe Thr Pro Lys Leu Gly Ser Val Gln Phe Ala
        355                 360                 365
Thr Asp Thr Asp Asn Asp Phe Glu Thr Gly Gln Asn Thr Arg Phe Thr
    370                 375                 380
Pro Val Gly Val Ile Gln Asp Gly Ser Ser Ala His Arg Asn Glu Pro
385                 390                 395                 400
Gln Gln Trp Val Leu Pro Asp Tyr Ser Gly Arg Thr Val His Asn Val
                405                 410                 415
His Leu Ala Pro Ala Val Ala Pro Thr Phe Pro Gly Glu Gln Leu Leu
            420                 425                 430
Phe Phe Arg Ser Thr Met Pro Gly Cys Ser Gly Tyr Pro Asn Met Asp
        435                 440                 445
Leu Asp Cys Leu Leu Pro Gln Glu Trp Val Gln His Phe Tyr Gln Glu
    450                 455                 460
Ala Ala Pro Ser Gln Ser Asp Val Ala Leu Leu Arg Phe Val Asn Pro
465                 470                 475                 480
Asp Thr Gly Arg Val Leu Phe Glu Cys Lys Leu His Lys Ala Gly Tyr
                485                 490                 495
Val Thr Val Ala His Thr Gly Gln His Asp Leu Val Ile Pro Pro Asn
            500                 505                 510
```

-continued

Gly Tyr Phe Arg Phe Asp Ser Trp Val Asn Gln Phe Tyr Thr Leu Ala
            515                 520                 525

Pro Met Gly Asn Gly Ala Gly Arg Arg Ala Leu
    530                 535                 540

<210> SEQ ID NO 8
<211> LENGTH: 540
<212> TYPE: PRT
<213> ORGANISM: Norovirus Hu/GII.4/Minerva/2006/USA

<400> SEQUENCE: 8

Met Lys Met Ala Ser Asn Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Glu Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Ser Arg Asn Tyr Thr Met Asn Leu Ala
    290                 295                 300

Ser Leu Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Lys Gly Asp Gly Ser Thr Arg Gly His Lys Ala Thr Val Tyr
            340                 345                 350

Thr Gly Ser Ala Pro Phe Thr Pro Lys Leu Gly Ser Val Gln Phe Ser
         355                 360                 365

Thr Asp Thr Glu Asn Asp Phe Glu Thr His Gln Asn Thr Lys Phe Thr
370                 375                 380

Pro Val Gly Val Ile Gln Asp Gly Ser Thr Thr His Arg Asn Glu Pro
385                 390                 395                 400

Gln Gln Trp Val Leu Pro Ser Tyr Ser Gly Arg Asn Val His Asn Val
             405                 410                 415

His Leu Ala Pro Ala Val Ala Pro Thr Phe Pro Gly Glu Gln Leu Leu
             420                 425                 430

Phe Phe Arg Ser Thr Met Pro Gly Cys Ser Gly Tyr Pro Asn Met Asp
         435                 440                 445

Leu Asp Cys Leu Leu Pro Gln Glu Trp Val Gln His Phe Tyr Gln Glu
450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
             485                 490                 495

Val Thr Val Ala His Thr Gly Gln His Asp Leu Val Ile Pro Pro Asn
             500                 505                 510

Gly Tyr Phe Arg Phe Asp Ser Trp Val Asn Gln Phe Tyr Thr Leu Ala
         515                 520                 525

Pro Met Gly Asn Gly Thr Gly Gly Arg Arg Ala Leu
530                 535                 540

<210> SEQ ID NO 9
<211> LENGTH: 540
<212> TYPE: PRT
<213> ORGANISM: Norovirus Hu/GII.4/cruiseship/2007/ZAF

<400> SEQUENCE: 9

Met Lys Met Ala Ser Ser Asp Ala Asn Pro Ser Asp Gly Ser Thr Ala
1               5                   10                  15

Asn Leu Val Pro Glu Val Asn Asn Glu Val Met Ala Leu Glu Pro Val
             20                  25                  30

Val Gly Ala Ala Ile Ala Ala Pro Val Ala Gly Gln Gln Asn Val Ile
         35                  40                  45

Asp Pro Trp Ile Arg Asn Asn Phe Val Gln Ala Pro Gly Gly Glu Phe
50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
             85                  90                  95

Asn Ser Tyr Ala Gly Gly Phe Glu Val Gln Val Ile Leu Ala Gly Asn
             100                 105                 110

Ala Phe Thr Ala Gly Lys Ile Ile Phe Ala Ala Val Pro Pro Asn Phe
         115                 120                 125

Pro Thr Glu Gly Leu Ser Pro Ser Gln Val Thr Met Phe Pro His Ile
130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
             165                 170                 175

Lys Leu Ile Ala Met Leu Tyr Thr Pro Leu Arg Ala Asn Asn Ala Gly
             180                 185                 190

```
Asp Asp Val Phe Thr Val Ser Cys Arg Val Leu Thr Arg Pro Ser Pro
            195                 200                 205
Asp Phe Asp Phe Ile Phe Leu Val Pro Pro Thr Val Glu Ser Arg Thr
        210                 215                 220
Lys Pro Phe Ser Val Pro Ile Leu Thr Val Glu Glu Met Thr Asn Ser
225                 230                 235                 240
Arg Phe Pro Ile Pro Leu Glu Lys Leu Phe Thr Gly Pro Ser Ser Ala
                245                 250                 255
Phe Val Val Gln Pro Gln Asn Gly Arg Cys Thr Thr Asp Gly Val Leu
            260                 265                 270
Leu Gly Thr Thr Gln Leu Ser Pro Val Asn Ile Cys Thr Phe Arg Gly
        275                 280                 285
Asp Val Thr His Ile Ala Gly Thr Gln Glu Tyr Thr Met Asn Leu Ala
    290                 295                 300
Ser Gln Asn Trp Asn Asn Tyr Asp Pro Thr Glu Glu Ile Pro Ala Pro
305                 310                 315                 320
Leu Gly Thr Pro Asp Phe Val Gly Lys Ile Gln Gly Val Leu Thr Gln
                325                 330                 335
Thr Thr Arg Arg Asp Gly Ser Thr Arg Gly His Lys Ala Thr Val Ser
            340                 345                 350
Thr Gly Ser Val His Phe Thr Pro Lys Leu Gly Arg Ile Gln Phe Ser
        355                 360                 365
Thr Asp Thr Ser Asn Asp Phe Glu Thr Gly Gln Asn Thr Arg Phe Thr
    370                 375                 380
Pro Val Gly Val Val Gln Asp Gly Ser Thr Thr His Gln Asn Glu Pro
385                 390                 395                 400
Gln Gln Trp Val Leu Pro Asn Tyr Ser Gly Arg Asp Ser His Asn Val
                405                 410                 415
His Leu Ala Pro Ala Val Ala Pro Ser Phe Pro Gly Glu Gln Leu Leu
            420                 425                 430
Phe Phe Arg Ser Thr Met Pro Gly Cys Ser Gly Tyr Pro Asn Met Asn
        435                 440                 445
Leu Asp Cys Leu Leu Pro Gln Glu Trp Val Gln His Phe Tyr Gln Glu
    450                 455                 460
Ala Ala Pro Ala Gln Ser Asp Val Ala Leu Leu Arg Phe Val Asn Pro
465                 470                 475                 480
Asp Thr Gly Arg Val Leu Phe Glu Cys Lys Leu His Lys Ser Gly Tyr
                485                 490                 495
Val Thr Val Ala His Thr Gly Gln His Asp Leu Val Ile Pro Pro Asn
            500                 505                 510
Gly Tyr Phe Arg Phe Asp Ser Trp Val Asn Gln Phe Tyr Thr Leu Ala
        515                 520                 525
Pro Met Gly Asn Gly Thr Gly Arg Arg Arg Ala Leu
    530                 535                 540

<210> SEQ ID NO 10
<211> LENGTH: 540
<212> TYPE: PRT
<213> ORGANISM: Norovirus Hu/GII.4/Armidale/NSW390I/2008/AU

<400> SEQUENCE: 10

Met Lys Met Ala Ser Asn Asp Ala Asn Pro Ser Asp Gly Ser Thr Ala
1               5                   10                  15
Asn Leu Val Pro Glu Val Asn Asn Glu Val Met Ala Leu Glu Pro Val
                20                  25                  30
```

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Thr Asn Ser
225                 230                 235                 240

Arg Phe Pro Ile Pro Leu Glu Arg Leu Tyr Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Ala Val Asn Ile Cys Thr Phe Arg Gly
        275                 280                 285

Asp Val Thr His Ile Ala Gly Ser Arg Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Arg Ser Asp Gly Ser Thr Arg Gly His Lys Ala Thr Val Leu
            340                 345                 350

Thr Gly Ser Ala Asp Phe Ala Pro Lys Leu Gly Arg Val Gln Phe Ala
        355                 360                 365

Thr Asp Thr Asp Asn Asp Phe Glu Ser Gly Gln Asn Thr Lys Phe Thr
    370                 375                 380

Pro Val Gly Val Ile Gln Asp Gly Ser Thr Thr His Arg Asn Glu Pro
385                 390                 395                 400

Gln Gln Trp Val Leu Pro Asn Tyr Ser Gly Arg Thr Gly His Asn Val
                405                 410                 415

His Leu Ala Pro Ala Val Ala Pro Thr Tyr Pro Gly Glu Gln Leu Leu
            420                 425                 430

Phe Phe Arg Ser Thr Met Pro Gly Cys Ser Gly Tyr Pro Asn Met Asp
        435                 440                 445

```
Leu Asp Cys Leu Leu Pro Gln Glu Trp Val Gln His Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
530                 535                 540

<210> SEQ ID NO 11
<211> LENGTH: 540
<212> TYPE: PRT
<213> ORGANISM: Norovirus Hu/GII.4/Stockholm/19865/2008/SE

<400> SEQUENCE: 11

Met Lys Met Ala Ser Asn Asp Ala Thr Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Ile Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285
```

```
Asp Val Thr His Ile Ser Gly Ser Arg Asn Tyr Thr Met Asn Leu Ala
    290                 295                 300

Thr Gln Asn Trp Asn Ser Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Ala Asp Gly Ser Thr Arg Gly His Lys Ala Thr Val Tyr
            340                 345                 350

Thr Gly Ser Ala Asp Phe Ala Pro Lys Leu Gly Arg Val Gln Phe Ala
        355                 360                 365

Thr Asp Thr Asp Asn Asp Phe Asp Ala Asn Gln Asn Thr Lys Phe Thr
    370                 375                 380

Pro Val Gly Val Ile Gln Asp Gly Asn Thr Ala His Arg Asn Glu Pro
385                 390                 395                 400

Gln Gln Trp Val Leu Pro Ser Tyr Ser Gly Arg Asn Ser His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540

<210> SEQ ID NO 12
<211> LENGTH: 540
<212> TYPE: PRT
<213> ORGANISM: Norovirus Hu/GII.4/New Orleans1805/2009/USA

<400> SEQUENCE: 12

Met Lys Met Ala Ser Ser Asp Ala Asn Pro Ser Asp Gly Ser Thr Ala
1               5                   10                  15

Asn Leu Val Pro Glu Val Asn Asn Glu Val Met Ala Leu Glu Pro Val
                20                  25                  30

Val Gly Ala Ala Ile Ala Ala Pro Val Ala Gly Gln Gln Asn Val Ile
            35                  40                  45

Asp Pro Trp Ile Arg Asn Asn Phe Val Gln Ala Pro Gly Gly Glu Phe
        50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125
```

```
Pro Thr Glu Gly Leu Ser Pro Ser Gln Val Thr Met Phe Pro His Ile
130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Pro Gly Ser Arg Asn Tyr Thr Met Asn Leu Ala
    290                 295                 300

Ser Gln Asn Trp Asn Ser Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asn Gly Ser Thr Arg Gly His Lys Ala Thr Val Tyr
            340                 345                 350

Thr Gly Ser Ala Asp Phe Ser Pro Lys Leu Gly Arg Val Gln Phe Ala
        355                 360                 365

Thr Asp Thr Asp Asn Asp Phe Glu Thr Asn Gln Asn Thr Lys Phe Thr
    370                 375                 380

Pro Val Gly Val Ile Gln Asp Gly Ser Thr Thr Pro Arg Asn Glu Pro
385                 390                 395                 400

Gln Gln Trp Val Leu Pro Ser Tyr Ser Gly Arg Asn Ile His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Ala Leu
    530                 535                 540
```

<210> SEQ ID NO 13
<211> LENGTH: 540
<212> TYPE: PRT
<213> ORGANISM: Norovirus Hu/GII.4/Sydney/NSW0514/2012/AU

<400> SEQUENCE: 13

Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

```
Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
            405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
            435                 440                 445

Leu Asp Cys Leu Leu Pro Gln Glu Trp Val Gln Tyr Phe Tyr Gln Glu
450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
            485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
            515                 520                 525

Pro Met Gly Asn Gly Thr Gly Arg Arg Arg Ala Val
530                 535                 540

<210> SEQ ID NO 14
<211> LENGTH: 548
<212> TYPE: PRT
<213> ORGANISM: Norovirus Hu/GII.3/1999

<400> SEQUENCE: 14

Met Lys Met Ala Ser Asn Asp Ala Ala Pro Ser Asn Asp Gly Ala Ala
1               5                   10                  15

Gly Leu Val Pro Glu Ile Asn Asn Glu Ala Met Ala Leu Asp Pro Val
            20                  25                  30

Ala Gly Ala Ala Ile Ala Ala Pro Leu Thr Gly Gln Gln Asn Ile Ile
        35                  40                  45

Asp Pro Trp Ile Met Asn Asn Phe Val Gln Ala Pro Gly Gly Glu Phe
50                  55                  60

Thr Val Ser Pro Arg Asn Ser Pro Gly Glu Val Leu Leu Asn Leu Glu
65                  70                  75                  80

Leu Gly Pro Glu Ile Asn Pro Tyr Leu Ala His Leu Ala Arg Met Tyr
            85                  90                  95

Asn Gly Tyr Ala Gly Gly Phe Glu Val Gln Val Leu Ala Gly Asn
        100                 105                 110

Ala Phe Thr Ala Gly Lys Val Ile Phe Ala Ala Ile Pro Pro Asn Phe
        115                 120                 125

Pro Ile Asp Asn Leu Ser Ala Ala Gln Ile Thr Met Cys Pro His Val
130                 135                 140

Ile Val Asp Val Arg Gln Leu Glu Pro Ile Asn Leu Pro Met Pro Asp
145                 150                 155                 160

Val Arg Asn Thr Phe Phe His Tyr Asn Gln Asp Ser Asp Ser Arg Leu
            165                 170                 175

Arg Leu Ile Ala Met Leu Tyr Thr Pro Leu Arg Ala Asn Asn Ser Gly
        180                 185                 190

Asp Asp Val Phe Thr Val Ser Cys Arg Val Leu Thr Arg Pro Ser Pro
        195                 200                 205

Asp Phe Ser Phe Asn Phe Leu Val Pro Pro Thr Val Glu Ser Lys Thr
210                 215                 220
```

-continued

```
Lys Leu Phe Thr Leu Pro Ile Leu Thr Ile Ser Glu Met Ser Asn Ser
225                 230                 235                 240

Arg Phe Pro Val Pro Ile Asp Ser Leu His Thr Ser Pro Thr Glu Asn
                245                 250                 255

Ile Val Val Gln Cys Gln Asn Gly Arg Val Thr Leu Asp Gly Glu Leu
                260                 265                 270

Met Gly Thr Thr Gln Leu Leu Pro Ser Gln Ile Cys Ala Phe Arg Gly
            275                 280                 285

Thr Leu Thr Arg Ser Thr Ser Arg Ala Ser Asp Gln Ala Asp Thr Pro
        290                 295                 300

Thr Pro Arg Leu Phe Asn His Arg Trp His Ile Gln Leu Asp Asn Leu
305                 310                 315                 320

Asn Gly Thr Pro Tyr Asp Pro Ala Glu Asp Ile Pro Ala Pro Leu Gly
                325                 330                 335

Thr Pro Asp Phe Arg Gly Lys Val Phe Gly Val Ala Ser Gln Arg Asn
                340                 345                 350

Pro Asp Ser Thr Thr Arg Ala His Glu Ala Lys Val Asp Thr Thr Ser
            355                 360                 365

Gly Arg Phe Thr Pro Lys Leu Gly Ser Leu Glu Ile Thr Thr Glu Ser
370                 375                 380

Asp Asp Phe Asp Thr Asn Gln Ser Thr Lys Phe Thr Pro Val Gly Ile
385                 390                 395                 400

Gly Val Asp Asn Glu Ala Glu Phe Gln Gln Trp Ser Leu Pro Asn Tyr
                405                 410                 415

Ser Gly Gln Phe Thr His Asn Met Asn Leu Ala Pro Ala Val Ala Pro
                420                 425                 430

Asn Phe Pro Gly Glu Gln Leu Leu Phe Phe Arg Ser Gln Leu Pro Ser
            435                 440                 445

Ser Gly Gly Trp Ser Asn Gly Val Leu Asp Cys Leu Val Pro Gln Glu
        450                 455                 460

Trp Val Gln His Phe Tyr Gln Glu Ser Ala Pro Ala Gln Thr Gln Val
465                 470                 475                 480

Ala Leu Val Arg Tyr Val Asn Pro Asp Thr Gly Arg Val Leu Phe Glu
                485                 490                 495

Ala Lys Leu His Lys Leu Gly Phe Met Thr Ile Ala Lys Asn Gly Asp
                500                 505                 510

Ser Pro Ile Thr Val Pro Pro Asn Gly Tyr Phe Arg Phe Glu Ser Trp
            515                 520                 525

Val Asn Pro Phe Tyr Thr Leu Ala Pro Met Gly Thr Gly Asn Gly Arg
        530                 535                 540

Arg Arg Ile Gln
545
```

UNITED STATES PATENT AND TRADEMARK OFFICE
CERTIFICATE OF CORRECTION

PATENT NO. : 11,566,050 B2
APPLICATION NO. : 16/756740
DATED : January 31, 2023
INVENTOR(S) : Lindesmith et al.

It is certified that error appears in the above-identified patent and that said Letters Patent is hereby corrected as shown below:

In the Specification

Column 9, Line 50: Please correct "N0224" to read --NO224--

Column 12, Lines 7-8: Please remove the paragraph break between '(Epitope Fs),' and 'wherein'

Column 28, Line 55: Please correct "GIL4F" to read --GII.4F--

Signed and Sealed this
Thirtieth Day of May, 2023

Katherine Kelly Vidal
*Director of the United States Patent and Trademark Office*